(12) United States Patent
Sevigny et al.

(10) Patent No.: US 7,276,208 B2
(45) Date of Patent: Oct. 2, 2007

(54) SAMPLE CARRIER HAVING SAMPLE TUBE BLOCKING MEMBER

(75) Inventors: Gerard J. Sevigny, Nashua, NH (US); Mark A. Talmer, West Ford, MA (US); Matthew W. Webb, Del Mar, CA (US); Gus G. Tseo, San Diego, CA (US)

(73) Assignee: Gen-Probe Incorporated, San Diego, CA (US)

(*) Notice: Subject to any disclaimer, the term of this patent is extended or adjusted under 35 U.S.C. 154(b) by 539 days.

(21) Appl. No.: 10/439,457

(22) Filed: May 16, 2003

(65) Prior Publication Data

US 2003/0215365 A1 Nov. 20, 2003

Related U.S. Application Data

(60) Provisional application No. 60/443,458, filed on Jan. 29, 2003, provisional application No. 60/381,551, filed on May 17, 2002.

(51) Int. Cl.
*B01L 9/00* (2006.01)
(52) U.S. Cl. .................. 422/104; 422/99; 422/102; 211/74
(58) Field of Classification Search ............ 422/62–66, 422/99, 102, 104; 436/43, 47–49; 211/74
See application file for complete search history.

(56) References Cited

U.S. PATENT DOCUMENTS

| | | | |
|---|---|---|---|
| 143,417 | A | 10/1873 | Munroe |
| 418,940 | A | 1/1890 | Bray |
| 1,168,595 | A | 1/1916 | Moltrum |
| 1,549,111 | A | 8/1925 | Grollman |
| 1,634,953 | A | 7/1927 | McCune et al. |
| D110,691 | S | 8/1938 | Dudley |
| 2,467,873 | A | 4/1949 | Weir |
| 2,708,037 | A | 5/1955 | Planeta |
| 2,741,913 | A | 4/1956 | Dovas |
| 2,902,170 | A | 9/1959 | Miller |
| 2,956,686 | A | 10/1960 | Garey |
| 2,979,210 | A | 4/1961 | Patterson |

(Continued)

FOREIGN PATENT DOCUMENTS

EP 0 100 663 A2 2/1984

(Continued)

*Primary Examiner*—Jill Warden
*Assistant Examiner*—Dwayne K. Handy
(74) *Attorney, Agent, or Firm*—Charles B. Cappellari

(57) ABSTRACT

A sample carrier comprising a lower support wall, a base joined to or in fixed proximity to a bottom end of the lower support wall, and sample tube receiving areas in fixed proximity to the lower support wall for receiving and holding a plurality of sample tubes in substantially vertical orientations. The sample carrier further comprising a blocking wall joined to a top end of the support wall which extends laterally over portions of sample tubes held by the sample carrier, thereby limiting vertical movement of the sample tubes during automated sampling procedures. The contents of sample tubes held by the sample carrier can be accessed by a robotic pipetting device. Additionally, a drip shield comprising a cover plate, a pair of through-holes for accessing sample tubes held by a the sample carrier, and a depending runner for maintaining the sample carrier on a sample carousel.

41 Claims, 24 Drawing Sheets

U.S. PATENT DOCUMENTS

| | | |
|---|---|---|
| 3,072,362 A | 1/1963 | Allen |
| 3,109,084 A | 10/1963 | Walsh |
| 3,115,247 A | 12/1963 | Hauser |
| 3,142,385 A | 7/1964 | Kahlenberg |
| 3,175,695 A | 3/1965 | Goodman et al. |
| 3,186,556 A | 6/1965 | Forsstrom |
| 3,375,934 A | 4/1968 | Bates |
| 3,390,783 A | 7/1968 | Quackenbush, Jr. |
| 3,474,913 A | 10/1969 | Jungner et al. |
| D216,491 S | 1/1970 | Brown |
| 3,605,829 A | 9/1971 | Genese et al. |
| 3,643,812 A | 2/1972 | Mander et al. |
| 3,680,967 A | 8/1972 | Englehardt |
| 3,698,563 A | 10/1972 | Gordon et al. |
| 3,744,661 A | 7/1973 | Fischer, Jr. |
| 3,752,651 A | 8/1973 | Bush |
| 3,765,538 A | 10/1973 | Kowert |
| 3,785,773 A | 1/1974 | Rohrbaugh |
| RE28,165 E | 9/1974 | McCormick |
| 3,904,035 A | 9/1975 | Metzler et al. |
| 3,905,482 A | 9/1975 | Knulst |
| 3,905,772 A | 9/1975 | Hartnett et al. |
| 3,909,203 A | 9/1975 | Young et al. |
| 3,960,271 A | 6/1976 | Nelson |
| 4,036,391 A | 7/1977 | Prodel |
| 4,043,762 A | 8/1977 | Olds |
| 4,055,396 A | 10/1977 | Meyer et al. |
| 4,124,122 A | 11/1978 | Emmitt |
| 4,160,803 A | 7/1979 | Potts |
| 4,202,634 A | 5/1980 | Kraft et al. |
| 4,207,289 A | 6/1980 | Weiss |
| 4,265,855 A | 5/1981 | Mandle et al. |
| 4,284,603 A | 8/1981 | Korom |
| 4,287,155 A | 9/1981 | Tersteeg et al. |
| 4,322,216 A | 3/1982 | Lillig et al. |
| D265,126 S | 6/1982 | Beall |
| 4,391,780 A | 7/1983 | Boris |
| 4,407,943 A | 10/1983 | Cole et al. |
| 4,422,555 A | 12/1983 | Jacobs |
| 4,434,890 A | 3/1984 | Sieck et al. |
| 4,438,068 A | 3/1984 | Forrest |
| 4,495,150 A | 1/1985 | Cook et al. |
| 4,510,119 A | 4/1985 | Hevey |
| 4,522,089 A | 6/1985 | Alvi |
| D280,130 S | 8/1985 | Harkins et al. |
| 4,534,465 A | 8/1985 | Rothermel et al. |
| D286,912 S | 11/1986 | Andersen |
| 4,639,135 A | 1/1987 | Borer et al. |
| D290,401 S | 6/1987 | Bjorkman |
| 4,751,052 A | 6/1988 | Schwartz et al. |
| 4,761,268 A | 8/1988 | Andersen et al. |
| 4,787,523 A | 11/1988 | Kalous |
| 4,805,772 A | 2/1989 | Shaw et al. |
| 4,824,641 A | 4/1989 | Williams |
| 4,849,177 A | 7/1989 | Jordan |
| 4,895,650 A | 1/1990 | Wang |
| 4,932,533 A | 6/1990 | Collier |
| 4,933,147 A | 6/1990 | Hollar et al. |
| 4,948,564 A | 8/1990 | Root et al. |
| 4,963,493 A | 10/1990 | Daftsios |
| 4,982,850 A | 1/1991 | Mears |
| 5,004,103 A | 4/1991 | Connors et al. |
| 5,006,066 A | 4/1991 | Rouse |
| 5,029,699 A | 7/1991 | Insley et al. |
| 5,057,282 A | 10/1991 | Linder |
| 5,077,013 A | 12/1991 | Guigan |
| 5,080,232 A | 1/1992 | Leoncavallo et al. |
| 5,082,631 A | 1/1992 | Lenmark, Sr. et al. |
| 5,098,663 A | 3/1992 | Berthold et al. |
| 5,108,287 A | 4/1992 | Yee et al. |
| 5,127,541 A | 7/1992 | Wakatake |
| 5,128,105 A | 7/1992 | Berthold et al. |
| 5,133,939 A | 7/1992 | Mahe |
| 5,137,693 A | 8/1992 | Mawhirt |
| 5,169,603 A | 12/1992 | Landsberger |
| 5,173,265 A | 12/1992 | Golias et al. |
| D333,522 S | 2/1993 | Gianino |
| 5,186,339 A | 2/1993 | Heissler |
| 5,191,975 A | 3/1993 | Pezzoli et al. |
| D336,219 S | 6/1993 | Held |
| 5,217,694 A | 6/1993 | Gibler et al. |
| 5,232,669 A | 8/1993 | Pardinas |
| 5,318,753 A | 6/1994 | Honda |
| 5,322,668 A | 6/1994 | Tomasso |
| 5,324,481 A | 6/1994 | Dunn et al. |
| 5,350,564 A | 9/1994 | Mazza et al. |
| 5,378,433 A | 1/1995 | Duckett et al. |
| 5,456,360 A | 10/1995 | Griffin |
| 5,456,882 A | 10/1995 | Covain |
| 5,472,669 A | 12/1995 | Miki et al. |
| 5,533,700 A | 7/1996 | Porter |
| 5,571,481 A | 11/1996 | Powell et al. |
| 5,579,928 A | 12/1996 | Anukwuem |
| 5,632,388 A | 5/1997 | Morrison et al. |
| 5,642,816 A | 7/1997 | Kelly et al. |
| 5,650,125 A | 7/1997 | Bosanquet |
| 5,651,941 A | 7/1997 | Stark et al. |
| 5,687,849 A | 11/1997 | Borenstein et al. |
| 5,700,429 A | 12/1997 | Buhler et al. |
| 5,704,495 A | 1/1998 | Bale et al. |
| 5,777,303 A | 7/1998 | Berney |
| D405,192 S | 2/1999 | Smith et al. |
| 5,897,090 A | 4/1999 | Smith et al. |
| 5,916,527 A | 6/1999 | Haswell |
| 5,931,318 A | 8/1999 | Shauo |
| D413,677 S | 9/1999 | Dumitrescu et al. |
| D414,273 S | 9/1999 | Smith et al. |
| 5,959,221 A | 9/1999 | Boyd et al. |
| D417,009 S | 11/1999 | Boyd |
| 5,985,219 A | 11/1999 | Lind |
| 5,993,745 A | 11/1999 | Laska |
| 5,996,818 A | 12/1999 | Boje et al. |
| 6,015,534 A | 1/2000 | Atwood |
| D420,747 S | 2/2000 | Dumitrescu et al. |
| D421,130 S | 2/2000 | Cohen et al. |
| 6,027,691 A | 2/2000 | Watts et al. |
| 6,065,617 A | 5/2000 | Cohen et al. |
| 6,123,205 A | 9/2000 | Dumitrescu et al. |
| D433,759 S | 11/2000 | Mathis et al. |
| 6,156,275 A | 12/2000 | Dumitrescu et al. |
| 6,190,619 B1 | 2/2001 | Kilcoin et al. |
| 6,193,064 B1 | 2/2001 | Finneran |
| D439,673 S | 3/2001 | Brophy et al. |
| 6,221,317 B1 | 4/2001 | Carl |
| 6,235,245 B1 | 5/2001 | Sherman et al. |
| 6,274,092 B1 | 8/2001 | Itoh |
| 6,335,166 B1 | 1/2002 | Ammann et al. |
| 6,618,981 B1 | 9/2003 | Rodriguez |
| 2002/0021983 A1 | 2/2002 | Comte et al. |
| 2002/0108917 A1 | 8/2002 | Maruyama |
| 2003/0017084 A1 | 1/2003 | Dale et al. |
| 2003/0215364 A1 | 11/2003 | Aviles et al. |

FOREIGN PATENT DOCUMENTS

| | | |
|---|---|---|
| EP | 0219802 A3 | 4/1987 |
| EP | 0919281 A2 | 6/1999 |
| EP | 0 965 385 A2 | 12/1999 |
| EP | 0965385 A2 | 12/1999 |
| JP | 1-161154 | 6/1989 |
| WO | WO93/01739 A1 | 2/1993 |

SAMPLE CARRIER HAVING SAMPLE TUBE BLOCKING MEMBER

CROSS-REFERENCE TO RELATED APPLICATIONS

This application claims the benefit of U.S. Provisional Application No. 60/381,551, filed May 17, 2002, and U.S. Provisional Application No. 60/443,458, filed Jan. 29, 2003, each of which applications is hereby incorporated by reference herein.

FIELD OF THE INVENTION

The present invention relates to a sample carrier for holding and containing a plurality of sample tubes. The sample carrier of the present invention is especially suited for use with an automated sampling system and sample tubes having penetrable caps. The present invention further relates to a drip shield for protecting against cross-contamination between sample tubes and for substantially limiting vertical movement of sample carriers positioned on conveying means during an automated sample transfer.

INCORPORATION BY REFERENCE

All references referred to herein are hereby incorporated by reference in their entirety. The incorporation of these references, standing alone, should not be construed as an assertion or admission by the inventors that any portion of the contents of all of these references, or any particular reference, is considered to be essential material for satisfying any national or regional statutory disclosure requirement for patent applications. Notwithstanding, the inventors reserve the right to rely upon any of such references, where appropriate, for providing material deemed essential to the claimed invention by an examining authority or court. No reference referred to herein is admitted to be prior art to the claimed invention.

BACKGROUND OF THE INVENTION

Procedures for determining the presence or absence of specific organisms or viruses in a test sample commonly rely upon nucleic acid-based probe testing. To increase the sensitivity of these tests, an amplification step is often included to increase the number of potential nucleic acid target sequences present in the test sample. There are many procedures for amplifying nucleic acids which are well known in the art, including, but not limited to, the polymerase chain reaction (PCR), (see, e.g., Mullis, "Process for Amplifying, Detecting, and/or Cloning Nucleic Acid Sequences," U.S. Pat. No. 4,683,195), transcription-mediated amplification (TMA), (see, e.g., Kacian et al., "Nucleic Acid Sequence Amplification Methods," U.S. Pat. No. 5,399,491), ligase chain reaction (LCR), (see, e.g., Birkenmeyer, "Amplification of Target Nucleic Acids Using Gap Filling Ligase Chain Reaction," U.S. Pat. No. 5,427,930), strand displacement amplification (SDA), (see, e.g., Walker, "Strand Displacement Amplification," U.S. Pat. No. 5,455,166), and loop-mediated isothermal amplification (see, e.g., Notomi et al., "Process for Synthesizing Nucleic Acid," U.S. Pat. No. 6,410,278). A review of several amplification procedures currently in use, including PCR and TMA, is provided in HELEN H. LEE ET AL., NUCLEIC ACID AMPLIFICATION TECHNOLOGIES (1997).

A concern with amplification is the possibility of cross-contamination, since transferring even a minute amount of target-containing sample to a target-negative sample could lead to the production of billions of target sequences in the "negative" sample. As a consequence, a test may indicate a positive result for a sample actually lacking nucleic acid from an organism or virus of interest. The source of a contaminating sample transfer may be an aerosol or bubbles released from a sample tube when a cap component of the sample tube is removed or penetrated by a practitioner or instrument. To minimize such sources of contamination, penetrable caps having filtering means were recently introduced and are disclosed by Anderson et al., "Collection Device and Method for Removing a Fluid Substance from the Same," U.S. Patent Application Publication No. US 2001-0041336 A1, and Kacian et al., "Penetrable Cap," U.S. Patent Application Publication No. US 2002-0127147 A1.

Components of penetrable caps generally exert a retention force against fluid transfer devices (e.g., pipette tips) as they are being withdrawn from corresponding sample tubes. See, e.g., Ammann et al., "Automated Process for Isolating and Amplifying a Target Nucleic Acid Sequence," U.S. Pat. No. 6,335,166 (an instrument for performing amplification assays on test samples which includes a robotic pipettor for obtaining test sample from a sample tube is disclosed). The retention force may be attributable to, for example, the sealing material of the cap and/or filtering means included within the cap. If the retention force is too great, a sample tube may be drawn out a sample carrier holding the sample tube by an exiting pipettor. In a more extreme case, the retention force of the cap and the sample tube holding force of the sample carrier are each great enough that the sample carrier is lifted vertically as the fluid transfer device is being withdrawn from the sample tube.

Conventional sample carriers commonly rely upon springs to immobilize distal ends of sample tubes, biasing the sample tubes against one or more opposing surfaces of the sample carriers. And more recently, a sample carrier has been described which further includes a top wall portion having a plurality of openings which are configured and arranged so that penetrable caps affixed to the vessel components of sample tubes are positioned snugly within the openings when the sample tubes are held by the sample carrier, thereby centering the sample tubes by restricting lateral movement of the corresponding caps within the openings. See Dale et al., "Sample Carrier and Drip Shield for Use Therewith," U.S. Patent Application Publication No. US 2003-0017084 A1. What these sample carriers lack, however, is a mechanism for ensuring that sample tubes remain in the sample carriers during automated sampling procedures when the retention force of a cap is greater than the holding force of the sample carrier on an associated vessel component. As a consequence, there is a risk that penetrable caps which exert too great a retention force against fluid transfer devices will be withdrawn, along with their associated vessel components, from sample carriers during automated sampling procedures. Thus, a need exists for a sample carrier capable of containing sample tubes having penetrable caps in their allotted positions on the sample carrier during automated sampling procedures.

SUMMARY OF THE INVENTION

The present invention solves the sample tube containment problem associated with known sample carriers by providing a sample carrier comprising a lower support wall, a base joined to or in fixed proximity to a bottom end of the lower support wall, and sample tube holding means in fixed proximity to the lower support wall for receiving and holding a plurality of sample tubes in substantially vertical orientations. The sample carrier further comprises a sample tube blocking member comprising a blocking wall joined directly or indirectly to a top end of the lower support wall, wherein the sample tube holding means is configured beneath the blocking wall of the sample tube blocking member such that the blocking wall extends over a portion of each sample tube held by the sample tube holding means, thereby limiting vertical movement of the sample tubes held by the sample carrier without obstructing access to the contents of the sample tubes by a robotic pipetting device. As used herein, the term "indirectly" means that there is intervening structure between and connecting the elements being joined.

In a preferred embodiment of the present invention, the sample carrier further comprises a transverse wall joined to the lower support wall, preferably an upper portion of the lower support wall. The sample tube blocking member of this embodiment further comprises an upper support wall depending from the blocking wall which is directly or indirectly joined to the transverse wall. The transverse wall includes a plurality of spaced-apart openings, where each opening is dimensioned to receive a sample tube therethrough, and where the openings are aligned with the sample tube holding means to maintain sample tubes held by the sample carrier in substantially vertical orientations. The openings are preferably circular in geometry, and the size of the openings may be the same or different to accommodate sample tubes having caps of equal or different diameters. Preferably, a top surface of the transverse wall is chamfered about the periphery of each of opening to facilitate insertion of the sample tubes into the sample tube holding means.

The openings of the transverse wall are preferably positioned so that at least a portion of the sample tube caps are contained within the openings between top and bottom surfaces of the transverse wall when the sample tubes are fully inserted into the sample tube holding means. Ideally, when portions of the caps are contained within the openings, the longitudinal axis of each cap should be no more than about 0.125 inches (3.18 mm) from the longitudinal axis of the corresponding opening and more preferably no more than about 0.1 inches (2.54 mm) from the longitudinal axis of the opening. Centering the caps prior to piercing them with a robotic pipetting device can aid in limiting the force required to penetrate the caps and, accordingly, can provide for more accurate pipetting.

In one embodiment of the present invention, the sample tube holding means comprises a series of sample tube receiving areas, each sample tube receiving area being defined by: (i) a pair of fixed partitions having a generally perpendicular or radial orientation relative to the lower support wall; (ii) one or more fixed retaining walls having an opposed orientation relative to the lower support wall; and (iii) one or more springs disposed within each of the sample tube receiving areas for holding a corresponding sample tube therein. In a preferred embodiment, the one or more springs employed to hold each sample tube in a corresponding sample tube receiving area comprises a leaf spring which is fixed by and extends outward relative to the support wall and into the sample tube receiving area. Preferably, the leaf spring extends outward through a slot formed in the lower support wall. The leaf spring is configured and arranged to bias the sample tube against the one or more retaining walls associated with the corresponding sample tube receiving area. The leaf spring may be chemically treated or physically altered to increase the coefficient of friction between the leaf spring and outer surfaces of the sample tubes. Regardless of the type of springs used, the springs preferably have a holding force of at least about 0.5 pounds force (2.22 N). The holding force should be sufficient to maintain sample tubes held by a sample carrier in a substantially vertical orientation and to prevent rotation of the sample tubes. As used herein, the phrase "holding force" refers to the force a spring exerts against a sample tube in a sample tube holding area, and the term "spring" is to be given its ordinary meaning, referring to an elastic device which substantially regains its original shape after being compressed.

In another embodiment of the present invention, the lower support wall is comprised of upper and lower portions and the sample tube holding means comprises a laterally extending wall positioned between and joined to upper and lower portions of the lower support wall. (The upper and lower portions of the lower support wall and the laterally extending wall may be separate components joined by any suitable attachment means (e.g., screws) or they may be integrally molded.) The laterally extending wall includes a plurality of spaced-apart openings, where each of the openings is dimensioned to receive a sample tube therethrough. The openings in the laterally extending wall are substantially axially aligned with the openings in the transverse wall. The base may include upwardly extending partitions having a generally perpendicular or radial orientation relative to the lower support wall which are positioned below and between adjacent openings in the laterally extending wall.

In a preferred embodiment, a set of finger springs may be provided to the laterally extending wall, where each set of finger springs depends from a bottom surface of the laterally extending wall about the periphery of one of the openings. Each set of finger springs in this embodiment is configured and arranged to hold a sample tube in a generally vertical orientation within the corresponding sample tube receiving area. A set of finger springs is preferably made up of four finger springs depending inwardly toward the longitudinal axis of the associated opening. A node having a curved end-surface at the distal end of each finger spring is preferred to facilitate removal of sample tubes after use.

In yet another embodiment of the present invention, the sample tube holding means comprises a series of slots formed in the base, where each slot is configured to receive a sample tube in a substantially vertical orientation. In a preferred embodiment, a vertical opening extending through an outer surface of the base adjacent each opening is provided to permit viewing of machine readable information (e.g., scannable bar code) affixed to an outer surface of a sample tube contained within a corresponding slot.

In still another embodiment of the present invention, the sample tube blocking member and the lower support wall or the transverse wall may be may be releasably joined to each other by means of mated first and second registration elements. In a preferred embodiment, the first registration elements consist of a pair of metal pins extending upward from a top surface of the lower support wall or the transverse wall, and the second registration elements consist of a pair of corresponding through-holes in the sample tube blocking member for receiving the pins therethrough. The pins may be adapted to include helical threads which extend above a top surface of the sample tube blocking member for receiving mated nuts for fixing the sample tube blocking member to the lower support wall or to the transverse wall. Because the sample carrier is preferably used in conjunction with a drip shield, such as the one described infra, the exposed portions of the pins are preferably contained entirely within the sample tube blocking member after joining the sample tube blocking member to the lower support wall or the transverse wall. Other releasable attachment means contemplated by the present invention include, by way of example only, clips, Velcro® or a snap-on arrangement.

In a further embodiment of the present invention, the partitions separating adjacent sample tube receiving areas extend outward from the lower support wall and upward from the base. In this embodiment, the retaining walls, which have an opposed orientation relative to the lower support wall, likewise extend upward from the base. By "an opposed orientation" is meant that the retaining walls have an orientation relative to the lower support wall other than radial or perpendicular. For certain embodiments, the retaining walls function to hold the sample tubes in the sample tube receiving areas against the force of the springs, while for other embodiments the retaining walls may simply aid in guiding sample tubes into the sample tube receiving areas. Although it is not a requirement that the partitions and retaining walls be joined to each other, the partitions and pairs of associated retaining walls are joined to each other in a preferred embodiment to form Y-shaped dividers. With the Y-shaped dividers, the partitions need not extend outward from the lower support wall.

Partitions at the ends of the sample carrier form a pair of end walls. (The end walls are also referred to as "partitions" herein to simplify the definition of a sample tube receiving area, even though end walls are not ordinarily understood to be partitions.) The end walls may serve as a surface for providing machine readable information (e.g., scannable bar code) about the contents of the sample tubes being carried by the sample carrier and/or about the number and types of assays to be performed on the contents of the sample tubes.

In yet a further embodiment of the present invention, the outer surface of the lower support wall includes a plurality of machine readable labels, each label being affixed to the lower support wall above the sample tube holding means and below the transverse wall or the sample tube blocking member. One such label is preferably positioned above each sample tube receiving area of the preferred sample carrier. The labels may include scannable bar codes or other machine readable information which can be used to indicate whether particular sample tubes are present in or absent from the sample tube holding means.

In still a further embodiment of the present invention, the sample tube holding means is capable of receiving and holding sample tubes on both sides of the lower support wall. In this embodiment, the blocking wall of the sample tube blocking member extends laterally away from both sides of the lower support wall. The blocking wall extends over only a portion of each sample tube on each side of the lower support wall, thereby permitting unobstructed access to the contents of the sample tubes by a robotic pipetting device.

The sample carrier of the present invention may have a rectilinear or arcuate shape, although an arcuate shape is preferred. The sample carrier is preferably has an arcuate shape for use on an automated sample carousel.

In another embodiment of the present invention, a drip shield is provided for use in an automated sampling system to protect the contents of sample tubes held by sample carriers from fluid contamination, especially hanging droplets which may be dislodged from a robotic pipetting device during an automated sampling procedure. By "automated sampling system" is meant a system for holding a sample tube in a substantially vertical orientation and conveying the sample tube by automated means to a location within an apparatus where the contents of the sample tube may be accessed by a robotic pipetting device in order to effect a transfer of at least a portion of the contents to another location within the apparatus. The drip shield of the present invention is preferably constructed of a substantially non-conductive material and includes a cover plate which may have an arcuate shape conforming to the arcuate shape of the preferred sample carrier.

The cover plate of the drip shield includes one or more through-holes, where each through-hole is configured and arranged to provide non-interfering, vertical passage of an aligned pipette tip therethrough. The through-holes are sized to permit access to the contents of only one sample tube at a time, where the sample tubes being accessed are present in a sample carrier positioned beneath the cover plate. In a preferred embodiment, the diameter of each through-hole is the same as or smaller than the smallest diameter of any sample tube held by the sample carrier to minimize opportunities for contaminating the sample carrier and its contents. A top surface of the cover plate may be chamfered or, alternatively, include a rim about the periphery of each through-hole. A chamfered through-hole could aid in redirecting a misaligned pipette tip through the through-hole, whereas a rimmed through-hole would provide a further barrier to fluid contamination of sample tubes. Because the sample carrier used in the preferred automated sampling system includes two sets of sample tube receiving areas on opposite sides of the lower support wall, the drip shield includes at least two through-holes in the cover plate which are configured and arranged to provide access to sample tubes on opposite sides of the support wall.

Depending from a bottom surface of the cover plate is at least one runner, an inner runner, which is configured and arranged to limit vertical movement of a sample carrier positioned beneath the drip shield. In the preferred embodiment, the drip shield further includes two outer runners depending from the bottom surface of the cover plate which are spaced-apart from the inner runner so that inner side walls of the outer runners and both side walls of the inner runner extend over sample tubes held by the sample carrier. This arrangement of runners will block vertical movement of a sample tube withdrawn from the sample tube holding means should the sample tube blocking member fail in its function.

In the preferred drip shield, the inner runner has a flat bottom surface which is substantially longitudinally or arcuately centered on the bottom surface of the cover plate. The ends of the inner runner may be tapered so that a sample carrier which is not fully seated in a sample carrier receiving well of a sample carousel may be progressively forced back into the corresponding sample carrier receiving well. The inner runner is preferably positioned so that the drip shield and the sample carrier are not in touching contact prior to accessing the sample tubes. The distance between the bottom surface of the inner runner and a top surface of the sample tube blocking member of a sample carrier conveyed thereunder is preferably no more than about 0.125 inches (3.12 mm).

In yet another embodiment of the present invention, an automated sampling system is provided which includes one or more of the above-described sample carriers having sample tube holding means for receiving sample tubes on both sides of the lower support wall, a sample carrier conveying means, and the above-described drip shield which is located above and in fixed relationship to sample carriers being transported thereunder.

These and other features, aspects, and advantages of the present invention will become apparent to those skilled in the art after considering the following detailed description, appended claims and accompanying drawings.

Figure 1:
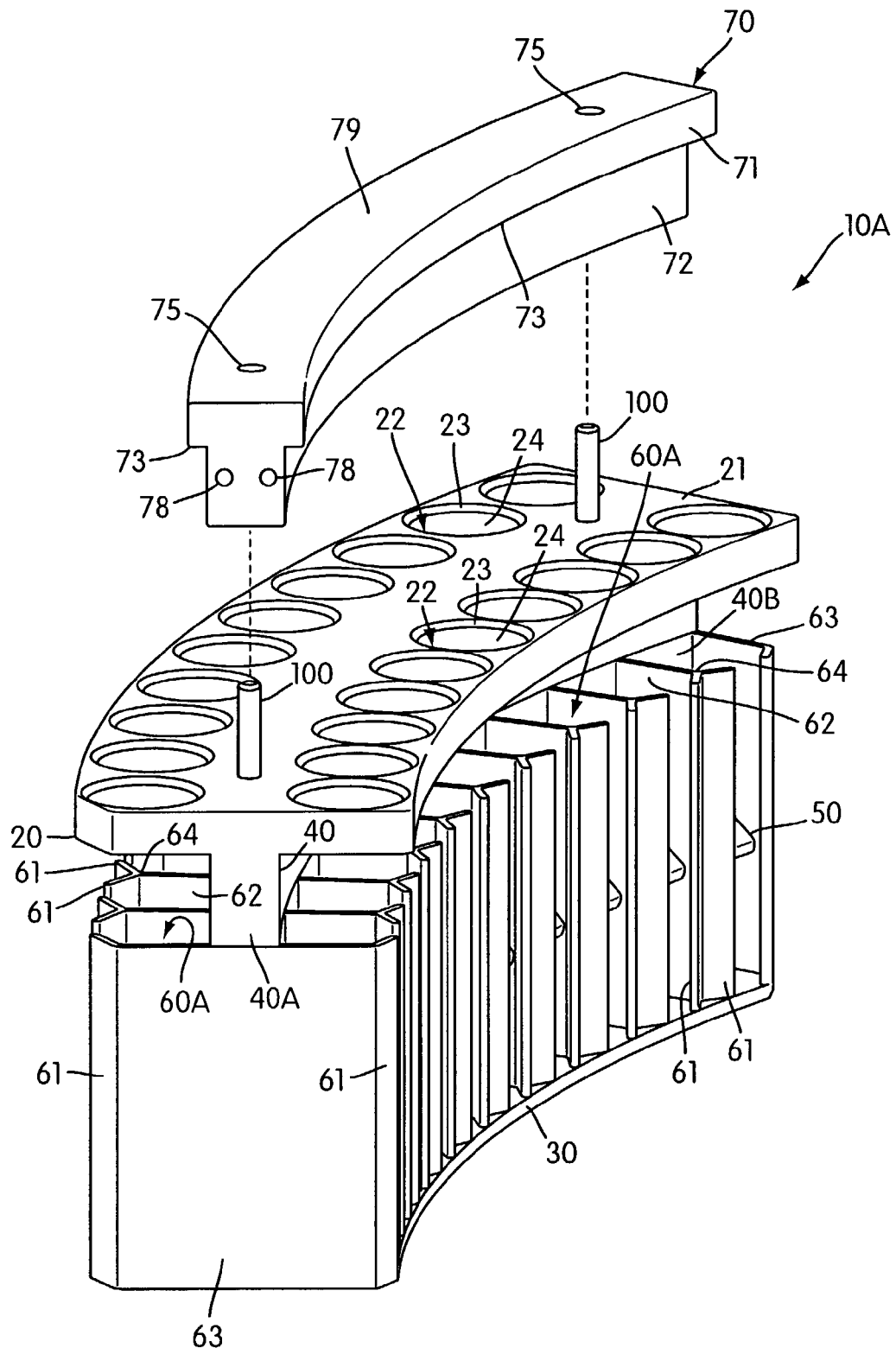
FIG. 1 is an exploded perspective view of a preferred sample carrier according to the present invention.

The sample carriers illustrated in the attached drawings include a number of redundant features. Where it would be clear to those skilled in the art from reviewing the drawings and reading the following description what features are being shown, the inventors have attempted to avoid including an excessive number of reference numbers by providing reference numbers for only a representative number of similar features depicted therein.

DETAILED DESCRIPTION OF THE PREFERRED EMBODIMENTS

While the present invention may be embodied in a variety of forms, the following description and accompanying drawings are merely intended to disclose some of those forms as specific examples of the present invention. Accordingly, the present invention is not intended to be limited to the forms or embodiments so described and illustrated. Instead, the full scope of the present invention is set forth in the appended claims.

With reference to the figures, preferred sample carriers 10 of the present invention are shown alone or in combination with a drip shield 200 for protecting against cross-contamination between sample tubes 300 carried by the sample carriers and for limiting vertical movement of the sample carriers when sample is being removed from any of the sample tubes. (Reference herein to a "sample carrier 10" is a general reference of to any of the illustrated sample carriers 10A-D.) Sample carriers 10 of the present invention are preferably used in combination with sample tubes 300 having sealed caps 310 which can be penetrated by standard pipette tips for use with positive displacement pipettes. To ensure proper alignment for penetrating these caps 310 and pipetting sample, the sample carriers 10 of the present invention substantially immobilize the sample tubes 300 they carry, thereby limiting both vertical and lateral movement of the sample tubes during sampling procedures. The sample tubes 300 used with the sample carriers 10 of the present invention may be transport tubes provided with sample collection kits which are used to receive and store samples for shipping and future analysis, including analysis with nucleic acid-based assays or immunoassays diagnostic for a particular pathogenic organism or virus. Such samples may include, for example, blood, urine, saliva, sputum, mucous or other bodily secretion, pus, amniotic fluid, cerebrospinal fluid, seminal fluid, tissue specimens, stool, environmental samples, food products, chemicals, powders, particles or granules. The sample tubes 300 may be of any shape or composition, provided vessel components 320 of the sample tubes are shaped to receive and retain the material of interest (e.g., animal, environmental, industrial, food or water samples). The vessel component 320 includes a closed end and an open end adapted for fixing the cap 310 thereto (e.g., mated helical threads). Preferred sample tubes are disclosed by Anderson et al., U.S. Patent Application Publication No. US 2001-0041336 A1, and Kacian et al., U.S. Patent Application Publication No. US 2002-0127147 A1. It is generally important that the composition of the sample tube 300 be essentially inert relative to the sample so that it does not significantly interfere with the performance or results of an assay.

As illustrated in FIG. 1, a particularly preferred sample carrier 10A according to the present invention includes a transverse wall 20, a base 30, a lower support wall 40 which joins the top wall and the base in fixed relationship, and a plurality of springs 50, where each spring is disposed within a sample tube receiving area 60. (Reference herein to a "sample tube receiving area 60" is a general reference of to any of the illustrated sample tube receiving areas 60A-C.) This preferred sample carrier 10A further includes a sample tube blocking member 70 having a laterally extending blocking wall 71 and a upper support wall 72 depending therefrom which is in touching contact with a top surface 21 of the transverse wall 20. The lower support wall 40 may be an integral component or it may comprise, for example, an upper portion 40A and a lower portion 40B, as shown in FIG. 1. In a preferred embodiment, the transverse wall 20 and the upper portion 40A of the lower support wall 40 form one integral component and the base 30 and the lower portion 40B of the lower support wall form another integral component, the two components being joined together by such means as a snap-fit, ultrasonic welding, adhesive, screws, clips or other mechanical fasteners.

Figure 8:
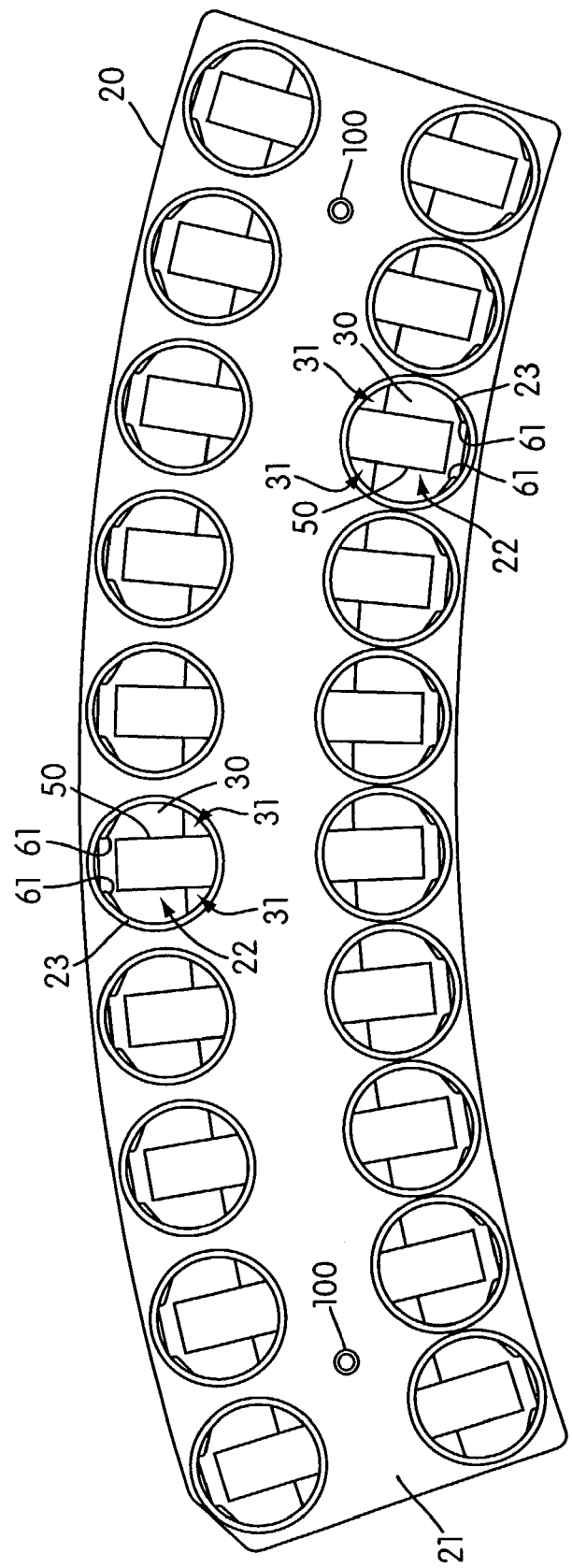
FIG. 8 is a top plan view of the sample carrier of FIG. 1 without the sample tube blocking member.

Spaced-apart openings 22 are included in the transverse wall 20 (see FIGS. 1 and 8) which may be of the same or different sizes and are dimensioned to receive sample tubes 300 into the sample carrier 10A. Each opening 22 is positioned above a sample tube receiving area 60, as described below. As illustrated in FIGS. 1 and 8, the transverse wall 20 includes a chamfered ring 23 circumscribing each opening 22 to facilitate insertion of the sample tubes 300 into the sample carrier 10A. An inner surface 24 of each opening 22 is preferably sized to receive the cap component 310 of the sample tube 300 in touching contact, which may be a frictional fit, preferably allowing the longitudinal axis of the cap component to move laterally from the longitudinal axis of the opening no more than about 0.125 inches (3.12 mm), and more preferably no more than about 0.1 inches (2.54 mm). Accordingly, in a preferred application the sample carrier 10A is dimensioned so that at least a portion of each cap 310 is contained within an opening 22 between top and bottom surfaces 21, 25 of the transverse wall 20 when the sample tubes 310 are fully inserted into the sample tube receiving areas 60. Restricting lateral movement of sample tubes held by the sample carrier 10A is particularly important when the sample tubes include penetrable caps, such as those disclosed by Anderson et al., U.S. Patent Application No. 20010041336 A1, and Kacian et al., U.S. Patent Application No. 20020127147 A1, because the caps may have structurally weakened centers or contain filters with centrally located passages or slits which must be penetrated by a pipette tip or other fluid transfer device associated with an automated sampling device.

The figures show a preferred embodiment in which the transverse wall 20 extends laterally in both directions relative to the lower support wall 40 and includes a series of openings 22 aligned along each side of the lower support wall. The number of openings 22 on each side of the lower support wall 40 is preferably 10. The present invention also contemplates sample carriers (not shown) which include a single series of openings 22 in the transverse wall 20, where the top wall extends laterally in only one direction relative to the lower support wall 40.

Figure 2:
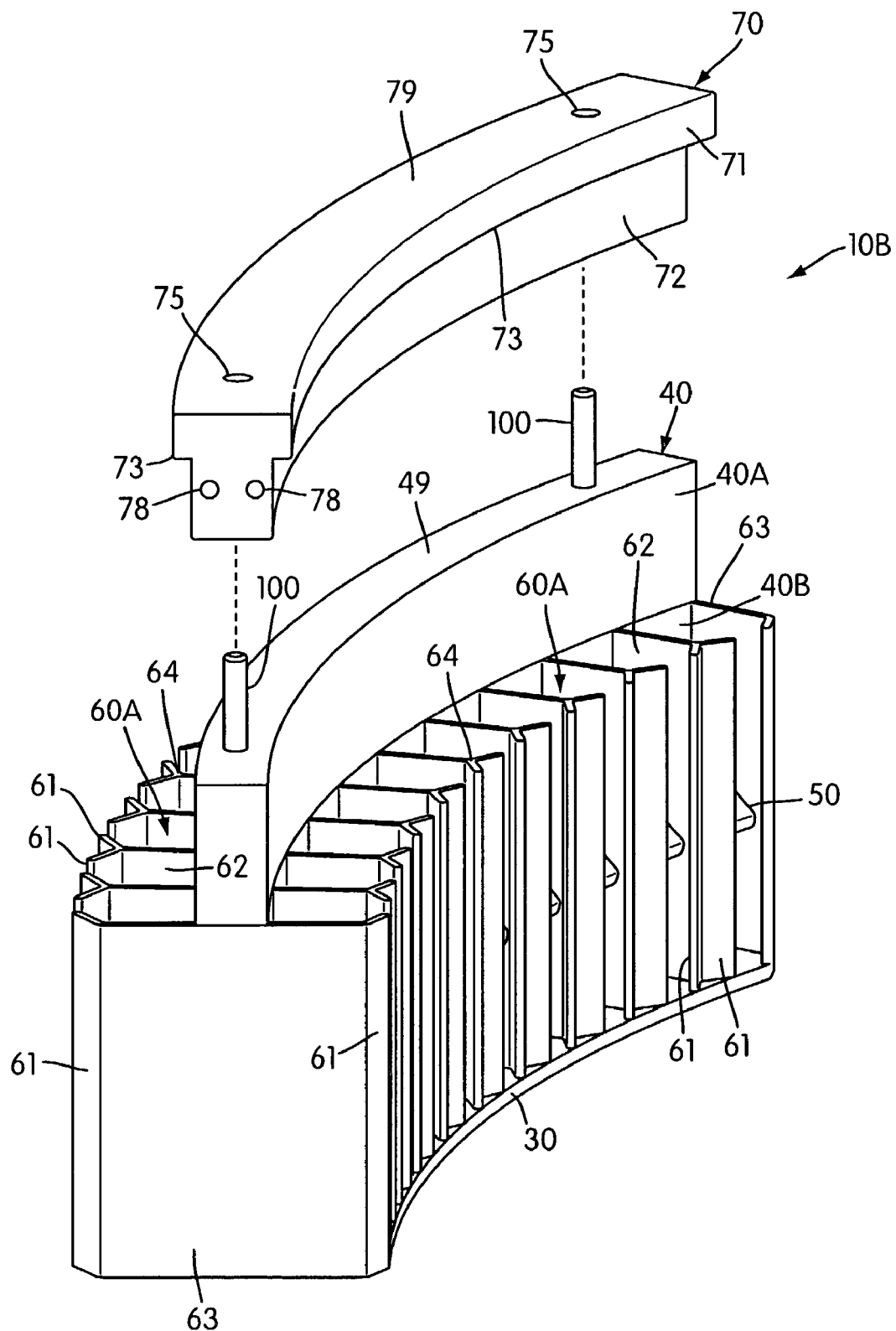
FIG. 2 is an exploded perspective view of another sample carrier according to the present invention.

FIG. 2 shows an alternative and less preferred sample carrier 10B in which the transverse transverse wall 20 is eliminated and the upper portion 40A of the lower support wall 40 and the sample tube blocking member 70 are joined directly. In this embodiment, the upper portion 40A of the lower support wall 40 extends higher than it does in the preferred sample carrier 10A to account for the lost thickness of the transverse wall 20. This sample carrier 10B is less preferred because it is more difficult to control lateral movement of the capped ends of the sample tubes 300.

Figure 6:
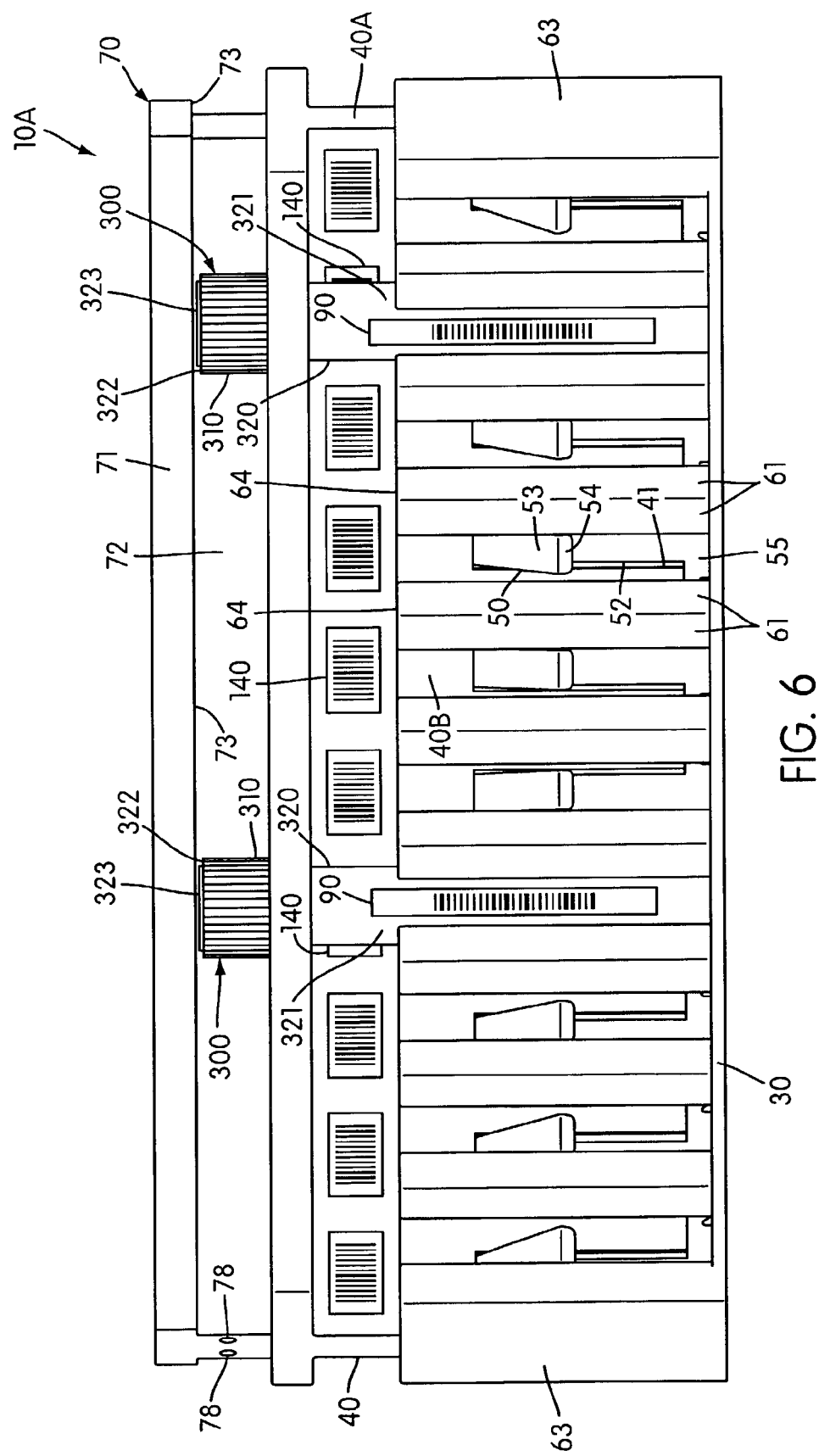
FIG. 6 is a front view of the sample carrier of FIG. 1 with two sample tubes inserted into sample tube receiving areas thereof.
Figure 7:
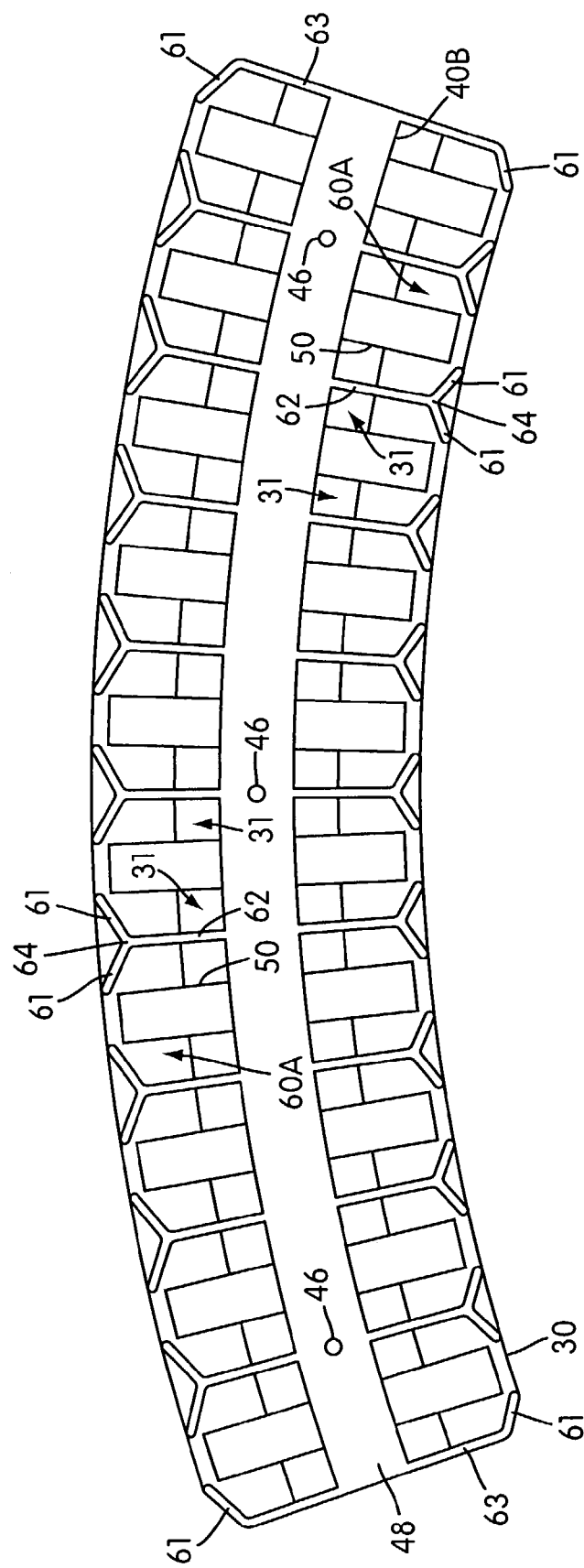
FIG. 7 is a top plan view of the sample carrier of FIG. 1 without a sample tube blocking member, and where a transverse wall and an upper portion of a lower support wall of the sample carrier are integrated.

As illustrated in the figures, the preferred sample carrier 10A includes a plurality of sample tube receiving areas 60A for receiving and positioning sample tubes 300 in substantially vertical orientations on the sample carrier (see, e.g., FIG. 6). In the preferred embodiment shown in FIG. 7, the sample tube receiving areas 60A include pairs of opposed retaining walls 61 extending upward from the base 30 and having angled orientations relative to the lower support wall 40. Each retaining wall 61 extends from a partition 62 separating two sample tube receiving areas 60A or an end wall 63, where the partition or end wall extends upward from the base and radially or perpendicularly outward from the lower portion 40B of the lower support wall 40. As depicted in FIGS. 1 and 7, each partition 62 and a pair of extending retaining walls 61 preferably form a solid Y-shaped divider 64. The inner angle of the "V" portion of the Y-shaped dividers 64 is preferably about 124° for those dividers on the outer radius and preferably about 116° for those dividers on the inner radius of the preferred arcuately shaped sample carrier 10A illustrated in FIGS. 1 and 7.

An opening 31 positioned in the base 30 of each sample tube receiving area 60A permits corrosive agents, such as bleach, to be drained from the sample carrier 10A. The use of these openings 31 also favorably minimizes the amount of material needed to form the sample carrier 10A.

Figure 3:
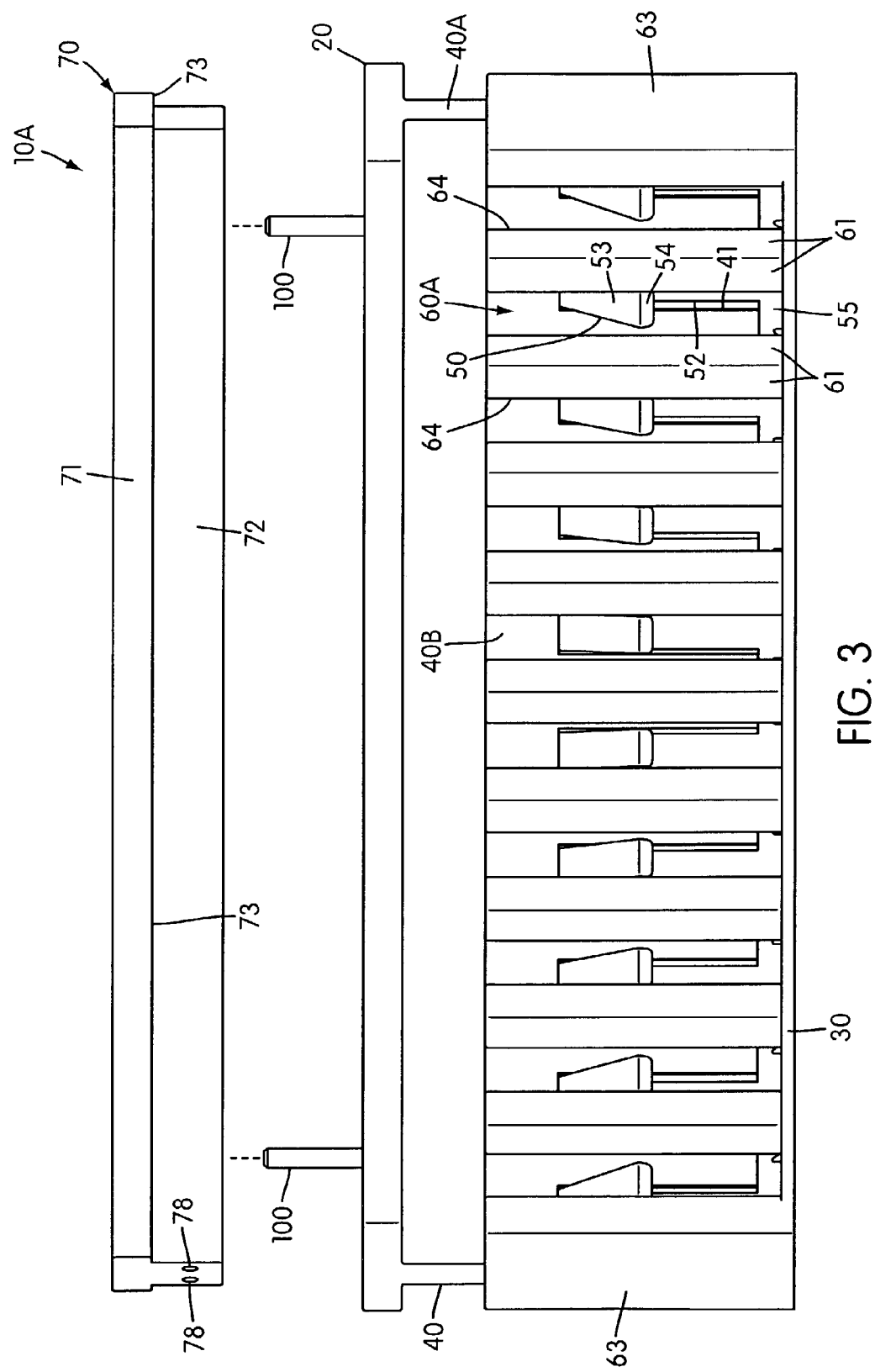
FIG. 3 is an exploded front view of the sample carrier of FIG. 1.
Figure 4:
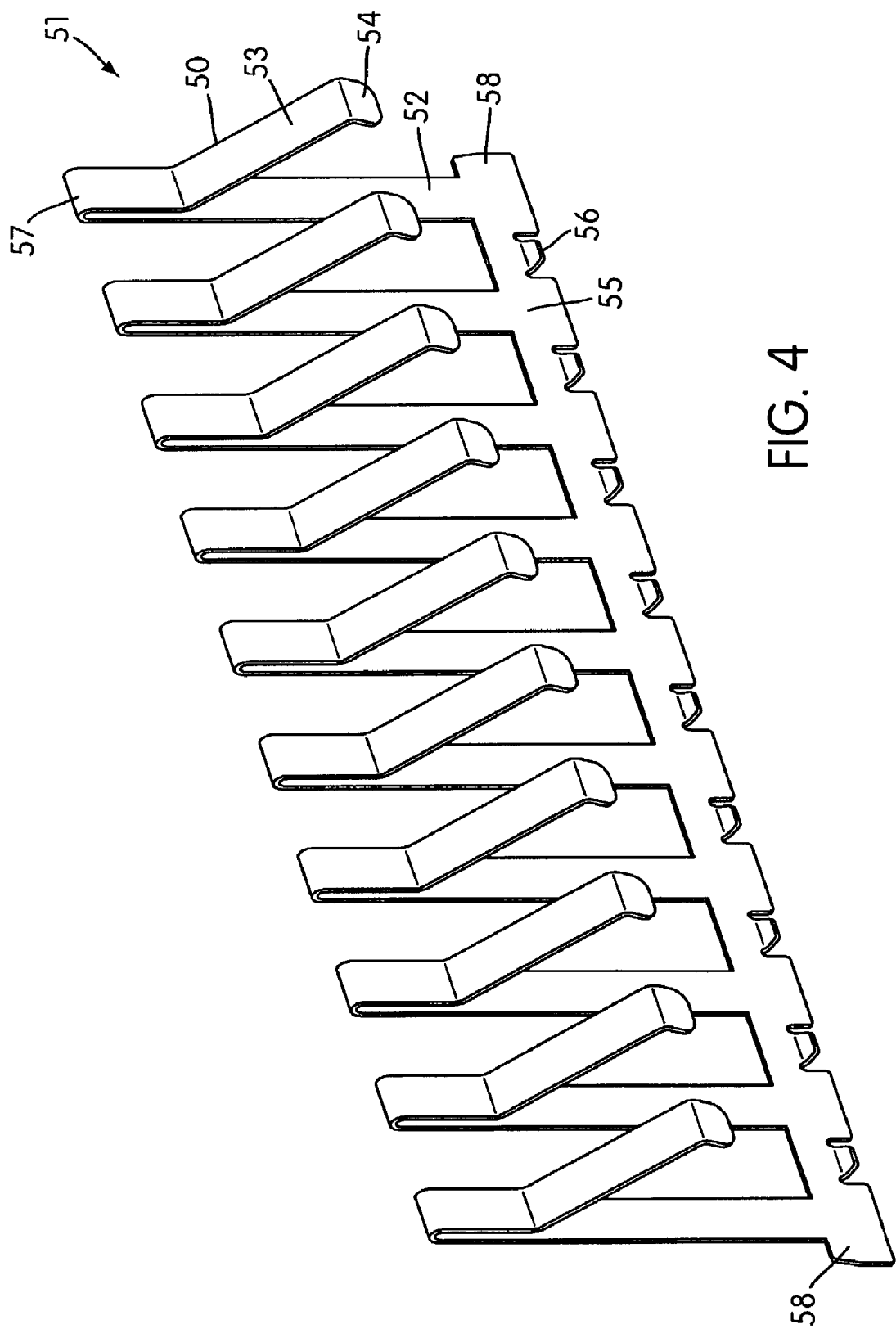
FIG. 4 is a perspective view of a spring cage of the sample carrier of FIG. 1.
Figure 5:
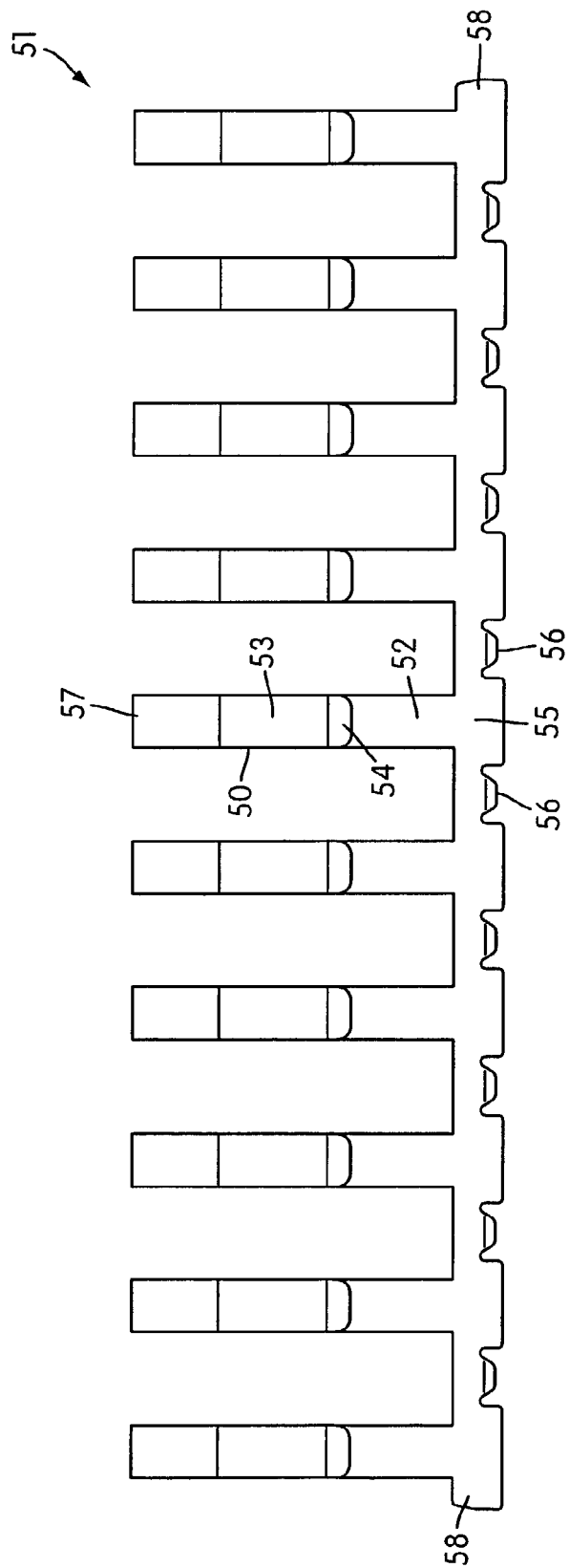
FIG. 5 is a front view of the spring cage of FIG. 4.

A spring 50 is disposed within each sample tube receiving area 60A of the sample carrier 10A. The preferred springs 50 are leaf springs made of stainless steel which extend outward from the lower portion 40B of the lower support wall 40 (see FIGS. 3, 6 and 7) through slots 41 formed therein and function to bias the sample tubes 300 against retaining walls 61 of sample tube receiving areas 60A. The preferred springs 50 form part of a pair of spring cages 51 comprising a plurality of springs (preferably 10), as shown in FIGS. 4 and 5. Each spring 50 of each spring cage 51 includes a vertical post 52 and a spring arm 53 extending downwardly and outwardly therefrom. The springs 50 are designed to provide a sufficient degree of tension to their respective sample tubes 300 to hold the sample tubes in an immobilized state as aliquots of sample are being removed from the sample tubes. The ends 54 of the spring arms 53 are rounded to facilitate insertion and removal of sample tubes 300 into corresponding sample tube receiving areas 60A.

Figure 11:
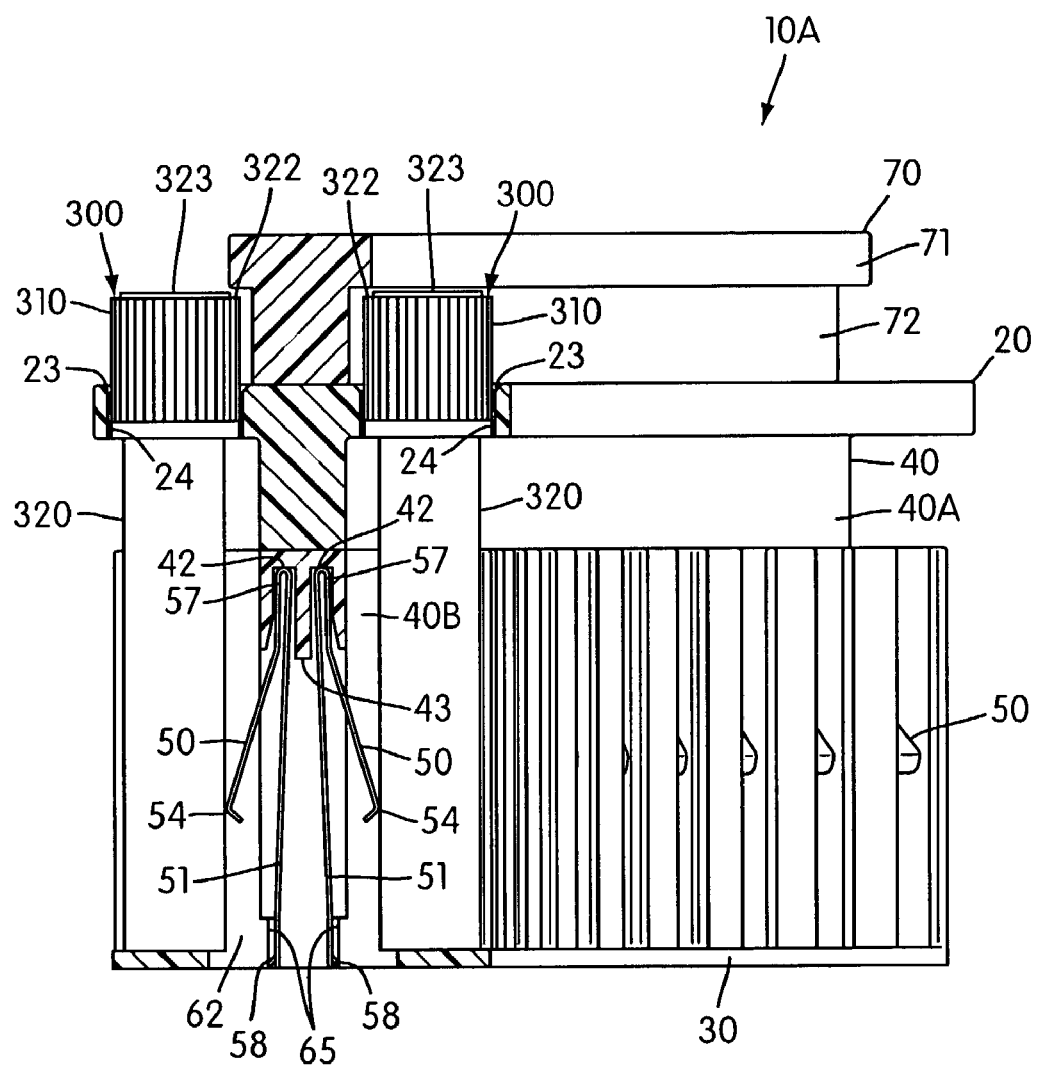
FIG. 11 is a section end view of the sample carrier of FIG. 9, taken along the 11—11 line thereof.

The holding force of each spring 50 is preferably at least about 0.5 pounds force (2.22 N). This force value was selected to be sufficient to maintain sample tubes 300 held by the sample carrier 10A in a substantially vertical orientation and to limit rotation of the sample tubes during use so that labels 90 applied to the sample tubes can be positioned for viewing within the sample carrier, as shown in FIG. 6. To increase the coefficient of friction between the springs 50 and outer surfaces 321 of the vessel components 320 of the sample tubes 300, the spring arms 53 may be physically or chemically altered, such as by sand-blasting or etching the surface of the spring arms using techniques well known in the art. The coefficient of friction should not be so great that the sample tubes 300 cannot be manually removed from the sample tube receiving areas 60A without difficulty. FIG. 11 provides a section side view of the preferred sample carrier 10A showing two sample tubes 300 which have been secured in the sample tube receiving areas 60A by the leaf springs 50.

Figure 12:
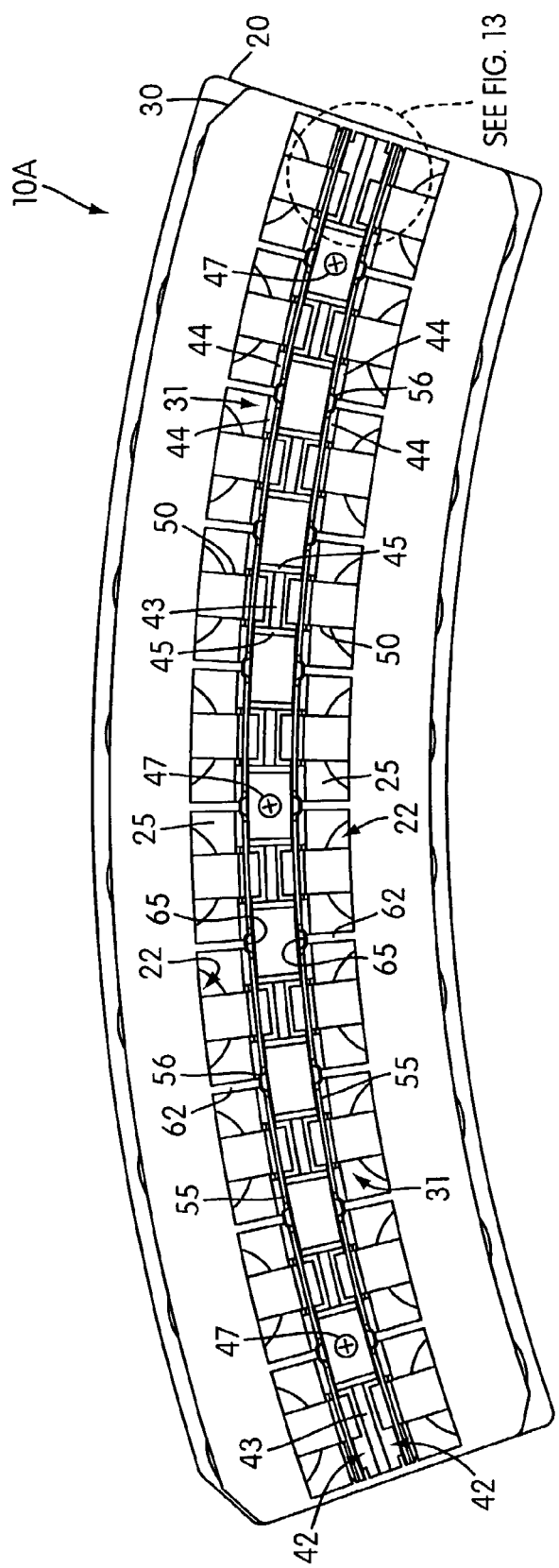
FIG. 12 is a bottom view of the sample carrier of FIG. 1.
Figure 13:
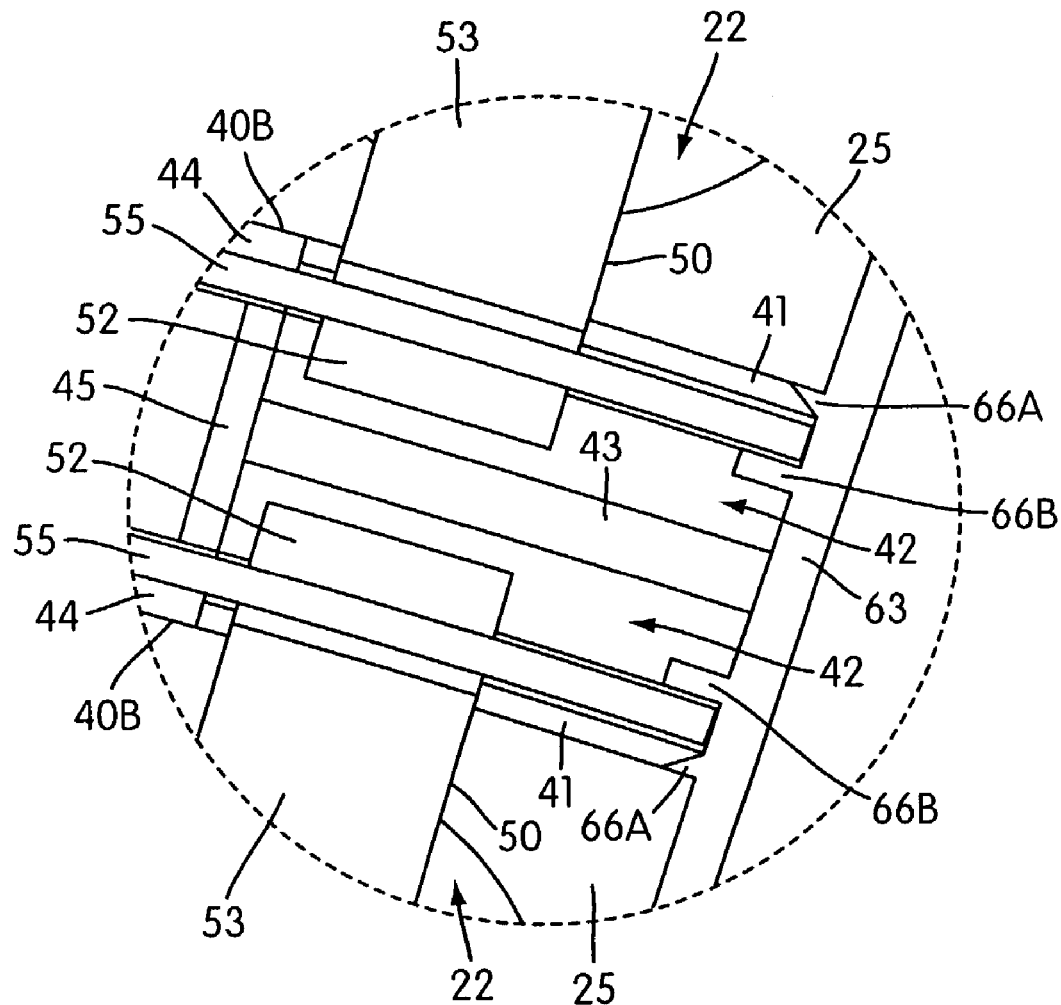
FIG. 13 is an enlarged partial bottom view of the sample carrier of FIG. 12 showing two sets of guide rails for inserting spring cages of FIG. 4 into the sample carrier.

The spring cages 51 include a base 55 for joining the vertical posts 52 to each other, as illustrated in FIGS. 4 and 5. Extending from each base 55 are a series of outwardly extending tabs 56 interspersed between the vertical posts 52, as illustrated in FIGS. 4 and 5. FIG. 12 shows that each tab 56 extends outwardly a sufficient distance to be in an interference fit with an inner surface 65 of one of the partitions 62 of the sample tube receiving area 60A when U-shaped elbows 57 of the spring cages 51 are inserted into recesses 42 formed in the lower portion 40B of the lower support wall 40, where pairs of opposed recesses are separated by a series of longitudinally or arcuately oriented dividing walls 43 (see FIG. 11). The spring cages 51 are moved into position from the base 40 of the sample carrier 10A by sliding a pair of end tabs 58 on each spring cage between opposed, parallel guide rails 66A, 66B which extend vertically and outwardly from each end wall 63, as depicted in FIGS. 12 and 13. Bottom surfaces 44 of the lower portion 40B of the lower support wall 40 make contact with and arrest movement of the base 55 when the spring cage 51 is in position. Inner walls 45 of the lower portion 40B of the lower support wall 40 keep the spring cages 51 spaced-apart and force the tabs 56 against the inner surfaces 65 of the partitions 62, thereby creating an interference fit which locks the spring cages into position within the sample carrier 10A.

Figure 15:
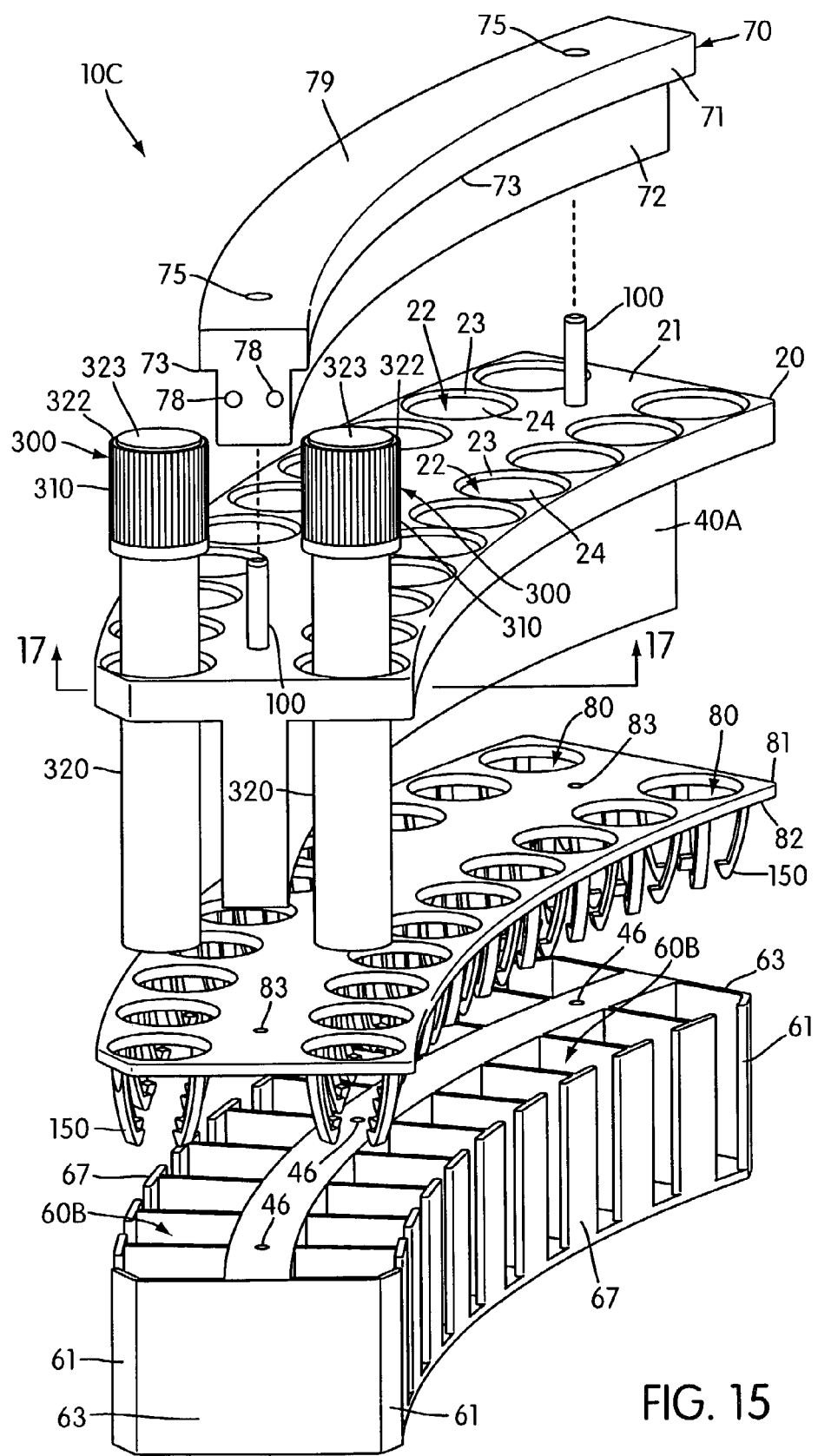
FIG. 15 is an exploded perspective view of another sample carrier according to the present invention with two sample tubes inserted into sample tube receiving areas.

In an alternative sample carrier 10C according to the present invention, a plurality of finger springs 150 substitute for each leaf spring 60 of the preferred sample carrier 10A, as shown in FIG. 15. In this embodiment, sets of equally-spaced finger springs 150 are arrayed about the periphery of openings 80 formed in a laterally extending wall 81 and depend from a bottom surface 82 thereof. The lateral wall 81 can bisect the lower support wall 40 into upper and lower portions 40A,B, as illustrated in FIG. 15. Any appropriate attachment means (e.g., screws 47) may be used to join together the lateral wall 81 and the upper and lower portions 40A,B of the lower support wall 40, however, it is preferred that aligned holes 83, 46 be provided in the lateral wall and a top wall 48 of the lower portion of the lower support wall for receiving screws therethrough which can be threadingly inserted into mated threads (not shown) provided in the upper portion of the lower support wall.

Figure 16:
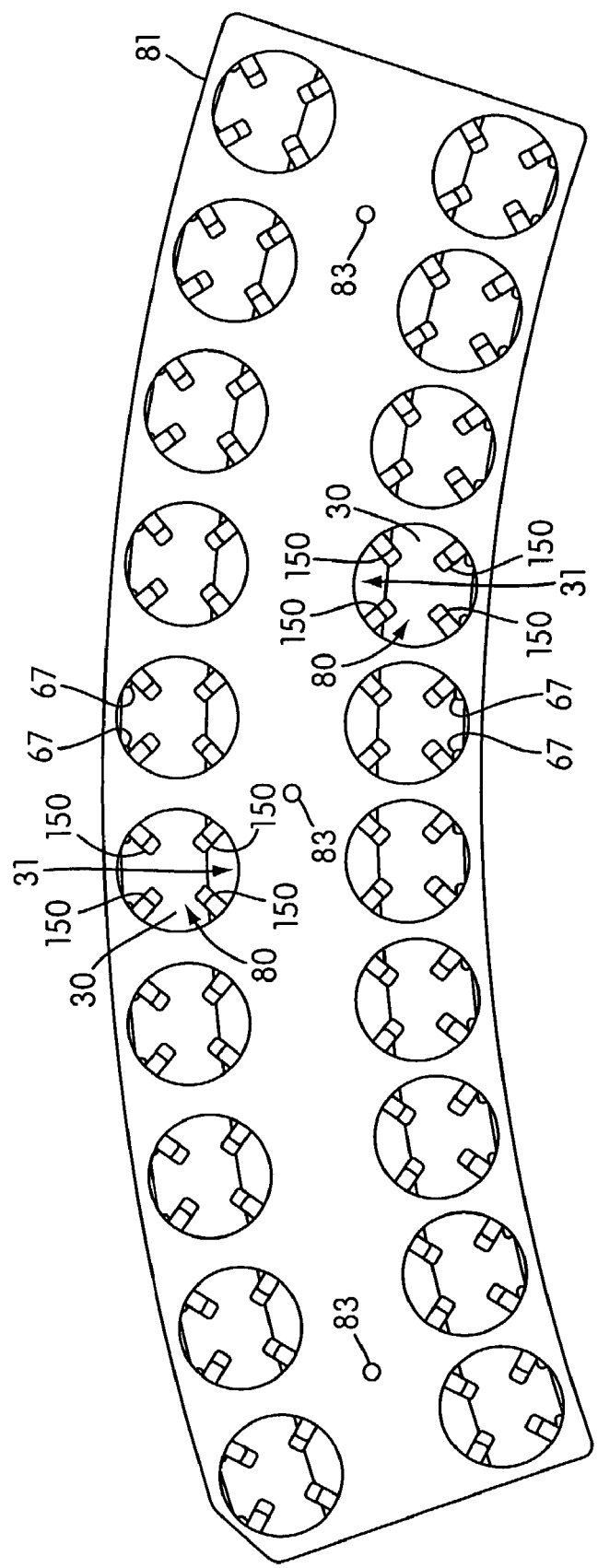
FIG. 16 is a top plan view of the sample carrier of FIG. 15 without the sample tube blocking member, and where the transverse wall and the upper portion of the lower support wall are integrated.
Figure 17:
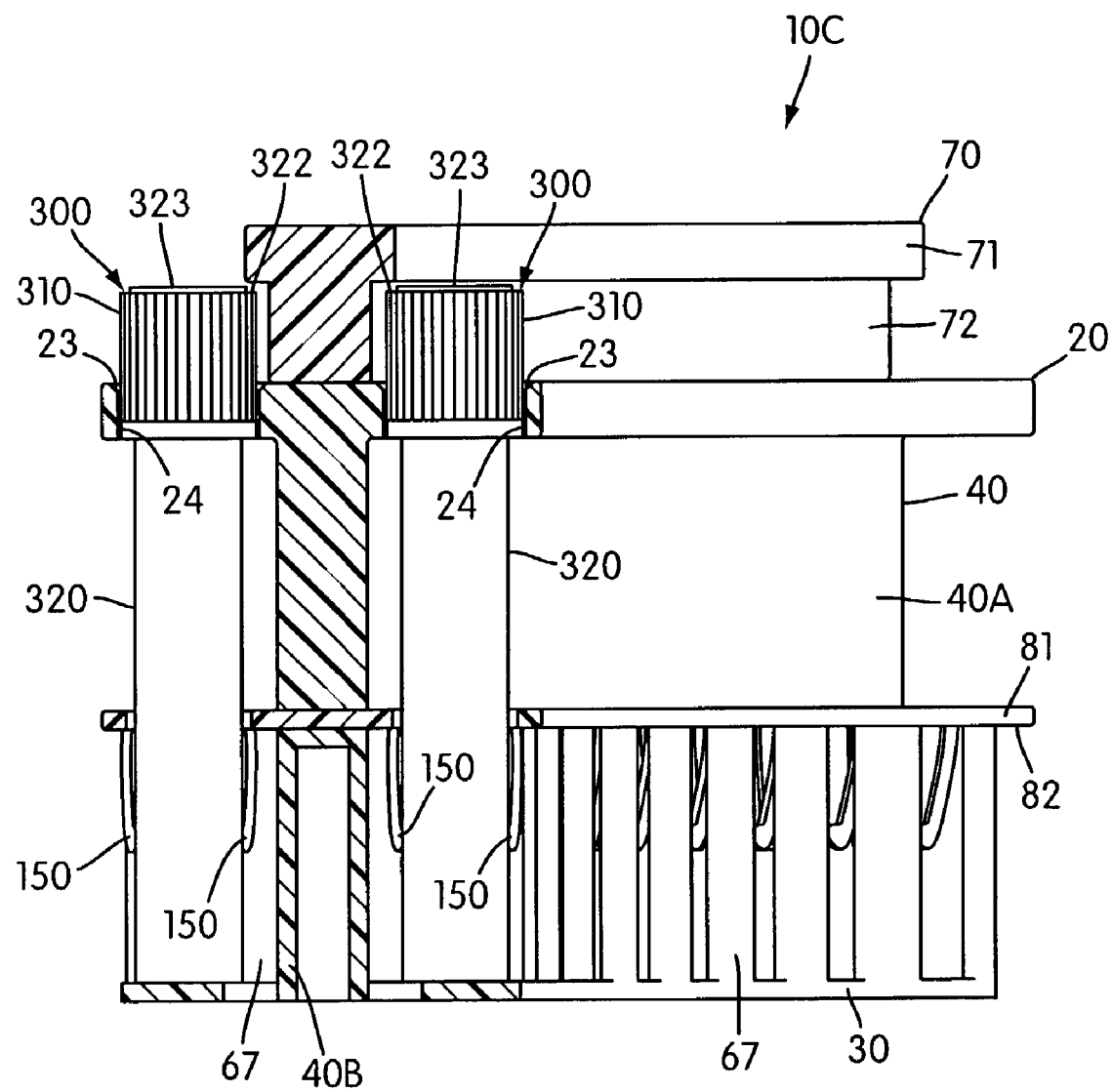
FIG. 17 is a section end view of the sample carrier of FIG. 15, taken along the 17—17 line thereof, and two sample tubes inserted into sample tube receiving areas.
Figure 18:
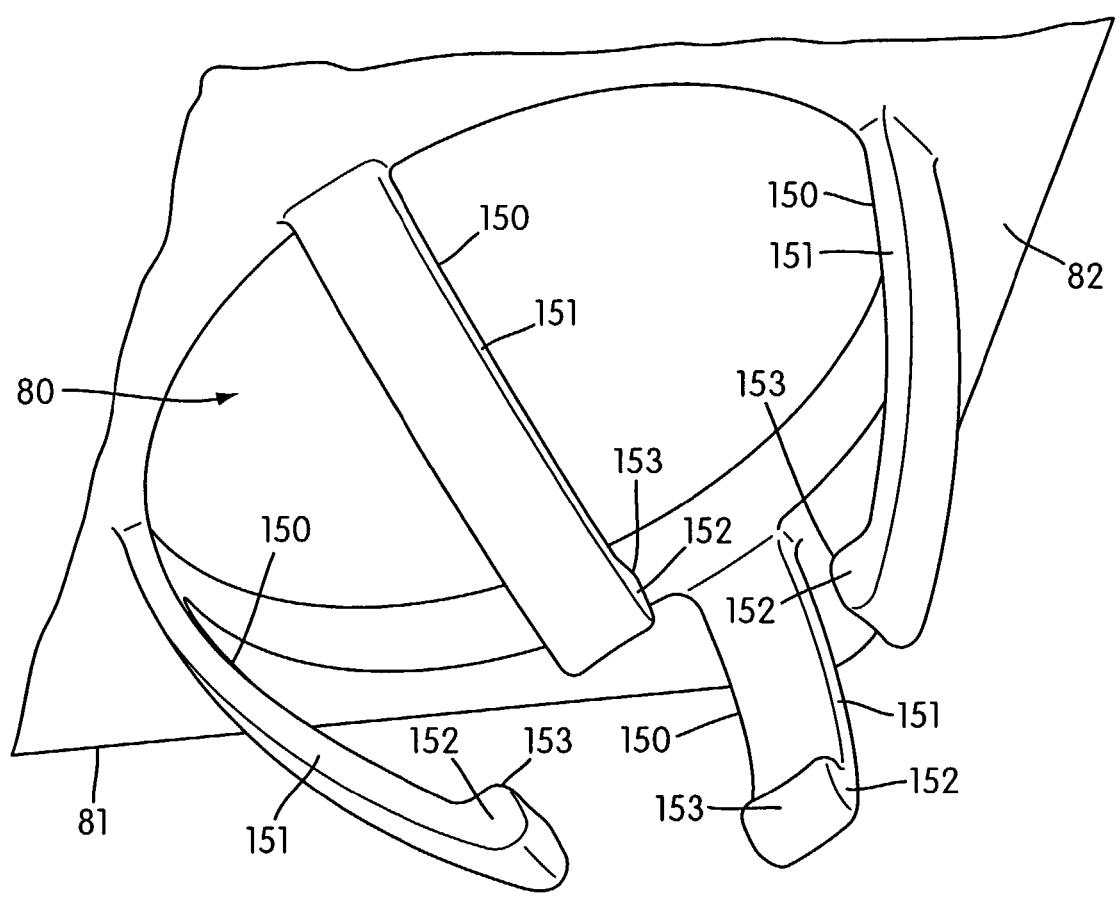
FIG. 18 is an enlarged partial perspective bottom view of the laterally extending wall of FIG. 15.

Each opening 80 in the laterally extending wall 81 is located above a sample tube receiving area 60B and is sized to receive the vessel component 320 of a sample tube 300 therethrough. Sets of finger springs 150 are preferably made up of four finger springs, as shown in FIG. 18, where each finger spring includes an inwardly sloping arm 151 and a distal node 152 having a curved end-surface 153 to facilitate removal of sample tubes 300 from the sample carrier 10C. The arrangement of each set of finger springs 150 about the periphery of an opening 80 should be such that the vessel component 320 of a sample tube 300 will be substantially centered within the corresponding opening 80 when the sample tube is inserted into the sample tube receiving area 60B. See FIG. 16. And, like the holding force of each leaf spring 50 in the preferred sample carrier 10A, the collective holding force of each set of finger springs 150 is preferably at least about 1.0 pound force (4.45 N), and more preferably at least about 1.5 pounds force (6.67 N). Also, to maintain sample tubes 300 held by the sample carrier 10C in a substantially vertical orientation during use, as illustrated in the side-section view of the sample carrier in FIG. 17, the openings 22 in the transverse wall 20 and the corresponding openings 80 in the lateral wall 81 are substantially co-axial.

While it is not necessary for holding and properly orienting sample tubes 300 in the sample carrier 10C, partitions, such as the T-shaped dividers 67 shown in FIG. 15, may be included for separating the sample tube receiving areas of the sample carrier 10C. When included, these dividers 67 preferably extend outward from the lower portion 40B of the lower support wall 40 and upward from the base 30 to the bottom surface 82 of the lateral wall 81, providing the lateral wall and the sample carrier 10C with additional rigidity.

Figure 19:
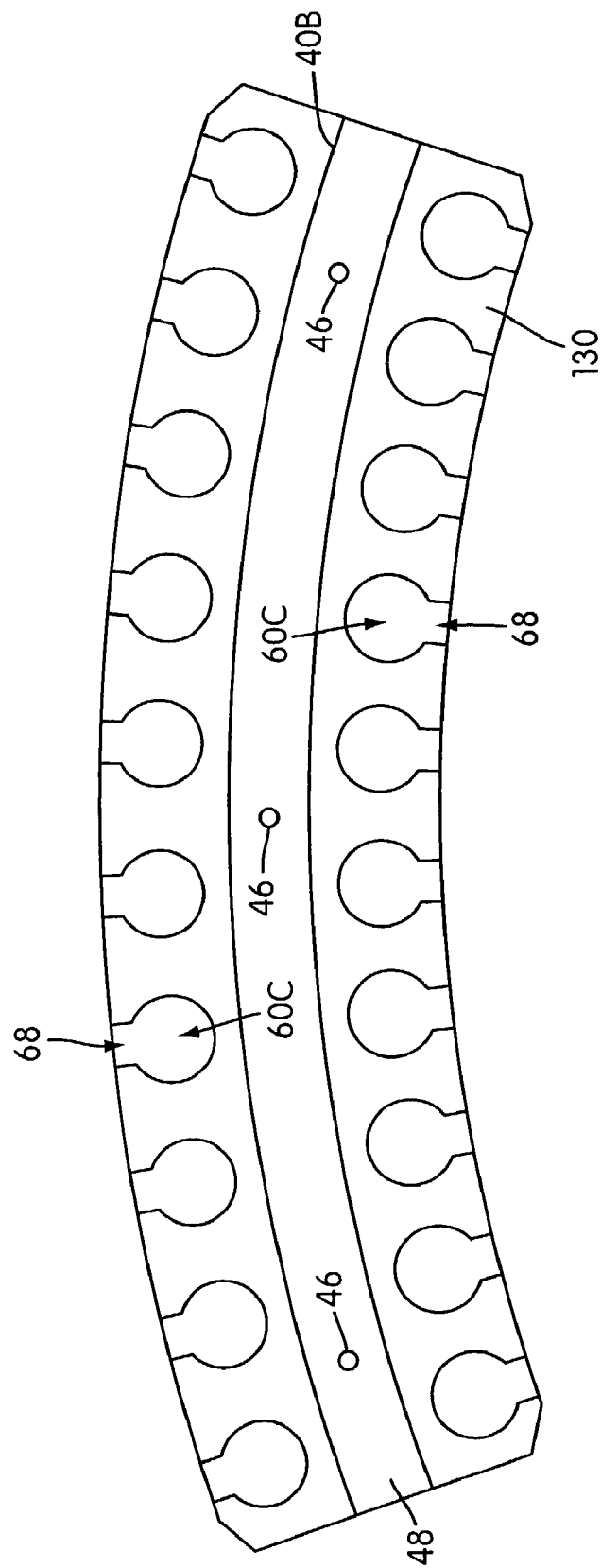
FIG. 19 is a top view of another sample carrier according to the present invention without the sample tube blocking member.
Figure 20:
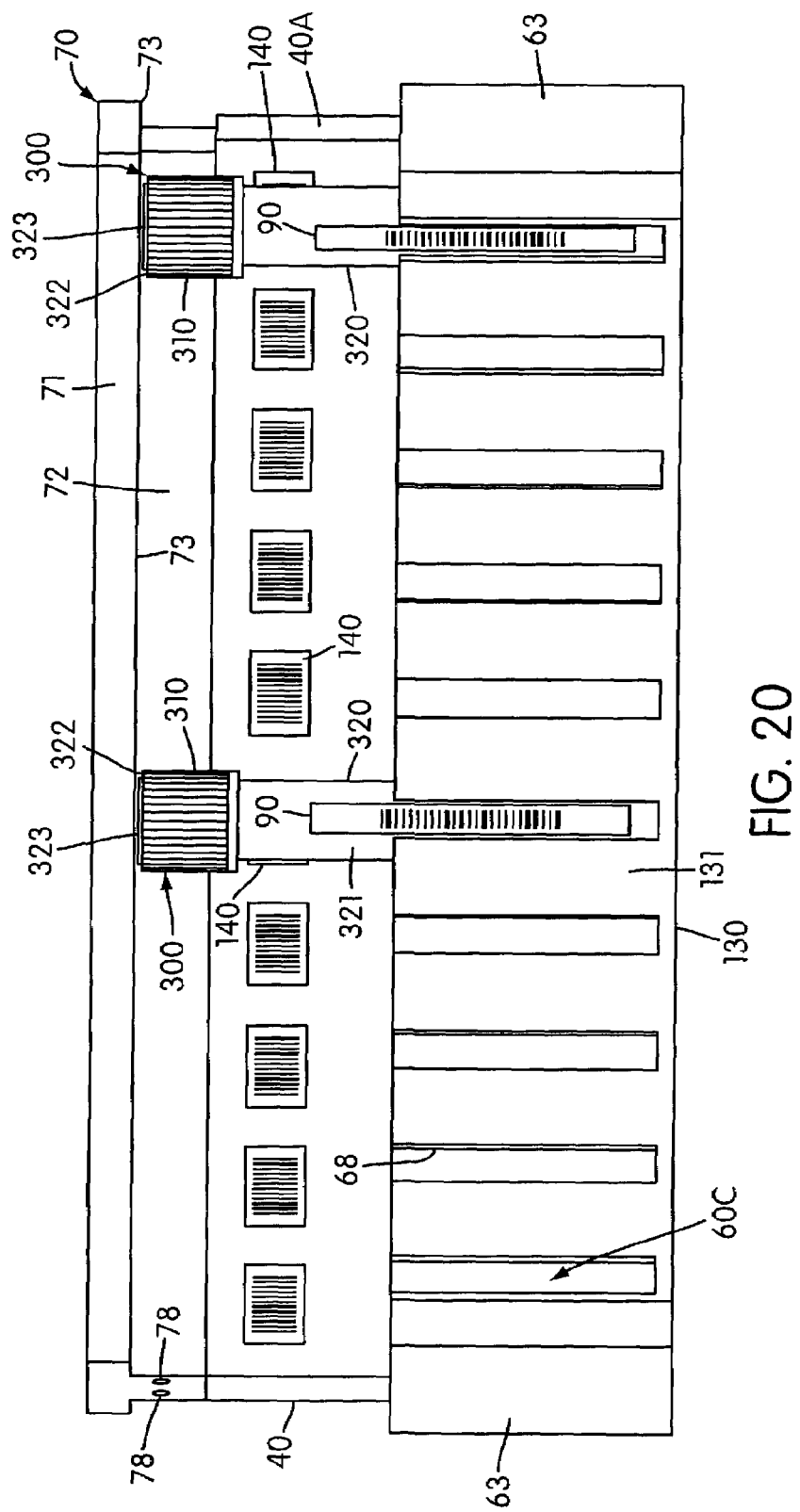
FIG. 20 is a front view of the sample carrier of FIG. 19 with the sample tube blocking member.

FIGS. 19 and 20 illustrate another sample carrier 10D according to the present invention, in which no springs are included for holding the sample tubes 300. Instead, a base 130 of the sample carrier 10D has slots 60C formed therein for receiving the sample tubes 300, where the slots constitute sample tube receiving areas. The slots 60C are preferably dimensioned to hold the sample tubes 300 in substantially vertical orientations. Vertical slits 68 extending through an outer surface 131 of the base 130 may be provided to permit viewing of machine readable labels 90 (e.g., scannable bar codes) present on sample tubes 300 held in the slots 60C. The labels 90 may provide information about, for example, the contents of the sample tubes 300 or assays to be performed on such contents.

In each of the sample carriers 10 illustrated in the figures, the sample tube blocking member 70 is provided to prevent sample tubes 300 from being removed from their corresponding sample tube receiving areas 60 during automated sampling. This feature is particularly important when the sample tubes 300 include caps 310 requiring penetration by a sampling device (e.g., robotic pipettor) since the friction between penetrated caps and sampling devices may overcome the holding forces of the sample tube receiving areas 60, resulting in partial or complete removal of sample tubes from the sample carriers 10 during sampling. Thus, the sample tube blocking member 70 serves as a fail-safe in the event that sample tube receiving areas 60 fail to maintain sample tubes 300 in the sample carriers 10 during sampling.

Figure 9:
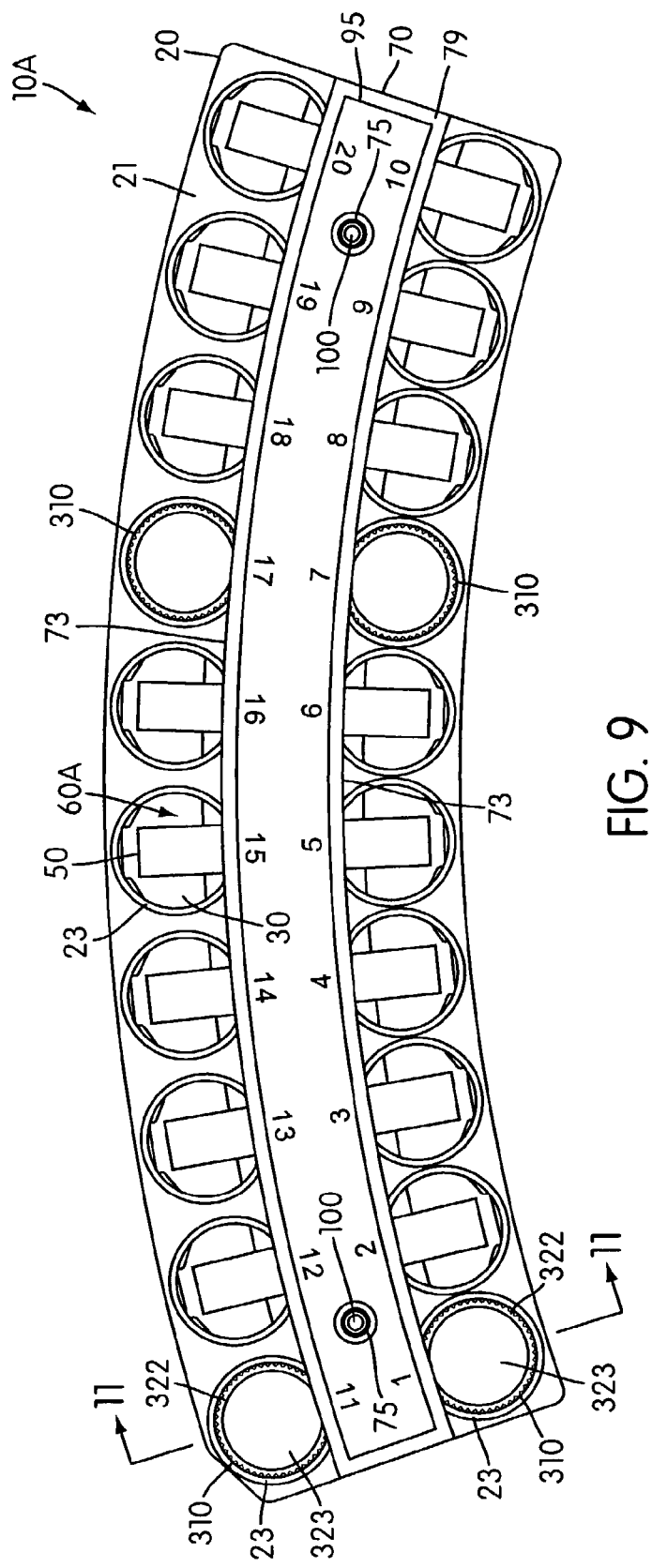
FIG. 9 is a top plan view of the sample carrier of FIG. 1 with four sample tubes inserted into sample tube receiving areas thereof.

As shown in FIG. 9, the blocking wall 71 includes at least one lateral edge 73 extending over at least a portion of the top rim 322 of the cap component 310 of one or more sample tubes 300 held by the sample carrier 10. A label 95 bearing alpha-numerical information may be applied to a top surface 79 of the blocking wall 71 to aid in identifying the locations of adjacent sample tubes 300, as depicted in FIG. 9. The illustrated caps 310 include penetrable seals 323 applied to the top rims for maintaining aerosol filters (not shown) within the caps. In the preferred embodiment, the blocking wall 71 includes two lateral edges 73, each lateral edge extending over a set of aligned sample tubes 300 on each side of the lower support wall 40 of the sample carrier 10. The distance that the lateral edges 73 extend over the sample tubes 300 is limited to permit non-interfering access to the contents of the sample tubes by a fluid transfer device (e.g., pipette tip) associated with an automated sampling device, such as a robotic pipettor.

A bottom surface 74 of the blocking wall 71 is preferably no more than about 0.1 inches (2.54 mm) above the top rim 322 of the cap component 310 of each sample tube 300 held by the sample carrier 10. Alternatively, the distance between the bottom surface 74 of the blocking wall 71 and the top rim 322 of the cap component 310 of each sample tube 300 is set so that the sample tubes cannot be fully withdrawn from the sample tube receiving areas 60 before their vertical movement is impeded by the blocking wall. While the upper support wall 72 depending from the blocking wall 71 serves to elevate the blocking wall above the transverse wall 20 of the sample carrier 10A,C embodiments shown in FIGS. 1 and 15, this feature would not be required in the sample carrier 10B,D embodiments shown in FIGS. 2 and 20, provided the height of the lower support wall 40 is adjusted to accommodate sample tubes 300 below the bottom surface 74 of the blocking wall 71.

Figure 10:
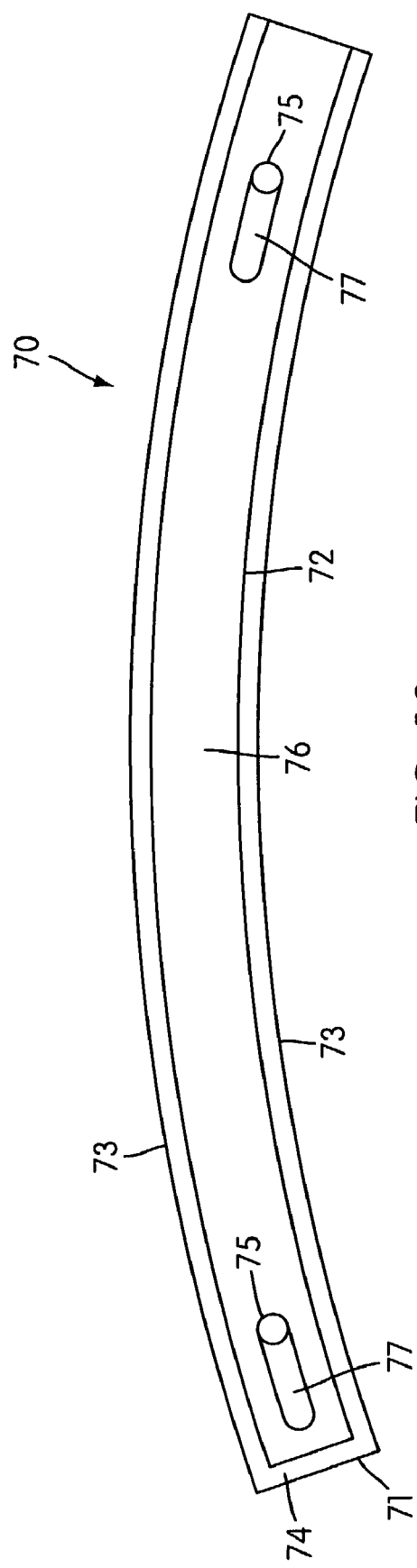
FIG. 10 is a bottom view of the sample tube blocking member of the sample carrier of FIG. 1.

FIGS. 1–3 and 15 illustrate preferred means for joining the sample tube blocking member 70 to the transverse wall 20 or the lower support wall 40. In these embodiments, a pair of metal pins 100 are fixed to the transverse wall 20 or the lower support wall 40 and extend upward from top surfaces 21, 49 thereof. These pins 100 are aligned with a pair of through-holes 75 which extend through the sample tube blocking member 70, as shown in FIG. 10. To aid in joining the sample tube blocking member 70 to the transverse wall 20 or the lower support wall 40, FIG. 10 also shows that a bottom surface 76 of the upper support wall 72 can be outfitted with a pair of channels 77 adjoining and arranged on the same side of the through-holes 75. Because the sample carriers 10 are preferably used in conjunction with drip shields 200, as described infra, it is not necessary to fixedly join the sample tube blocking member 70 to the transverse wall 20 or the lower support wall 40 prior to use. However, in applications where a drip shield of the type described below will not be used, it will be necessary to attach the sample tube blocking member 70 to the traverse wall 20 or the lower support wall 40 using mechanical fasteners (e.g., screws) if the sample tube blocking member is to achieve its sample tube containment function.

Figure 14:
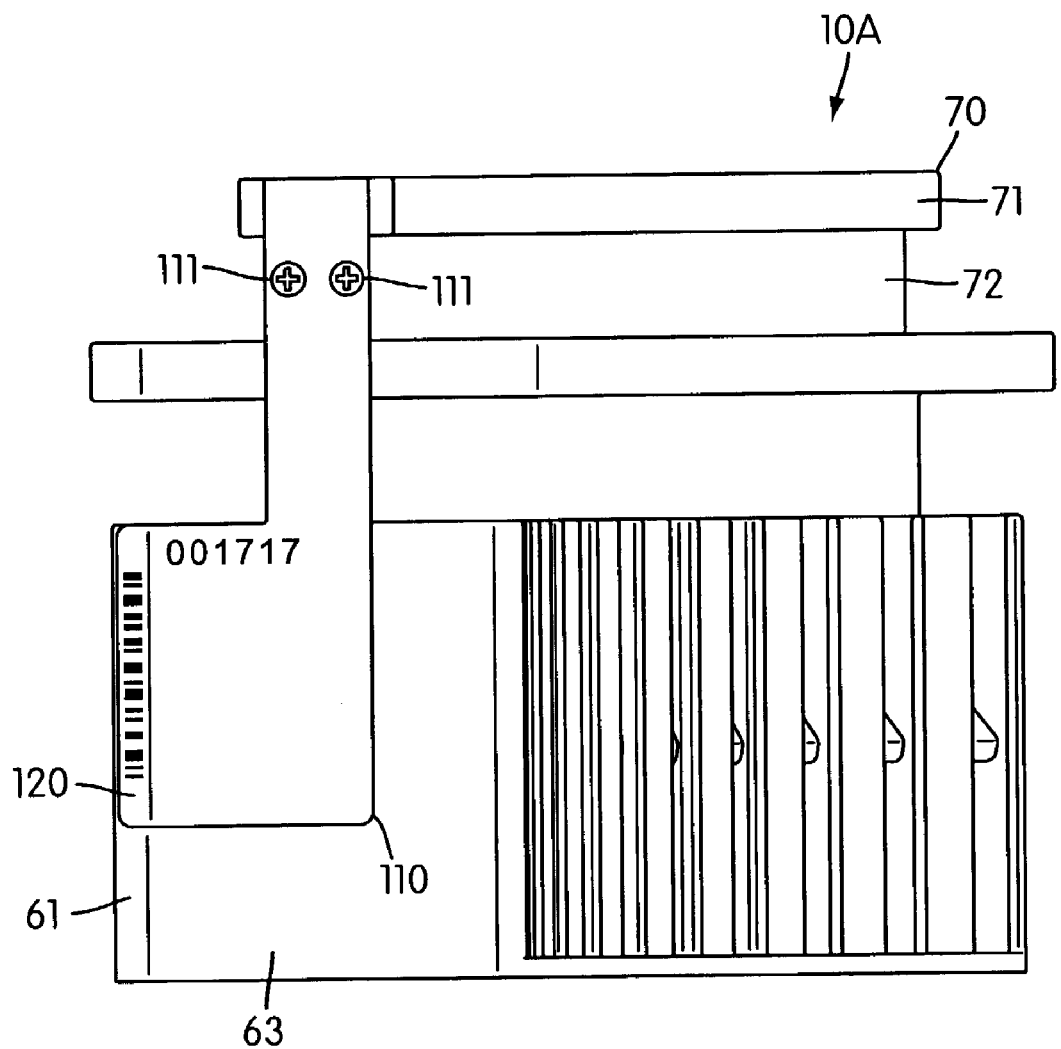
FIG. 14 is an end view of the sample carrier of FIG. 1 with an identification plate attached thereto.

FIG. 14 shows an identification plate 110 attached to the sample tube blocking member 70 which includes a label 120 providing machine readable (i.e., bar code) and/or alpha-numerical information. This information may inform an instrument or user of, for example, the presence or location of a particular sample carrier 10 in the instrument, the source of samples being carried by the sample carrier and/or the types of assays to be performed on the samples. The plate 110 may be fixed to the upper support wall 72 of the sample tube blocking member 70 by means of screws 111 threadingly inserted into mated screw holes 78 shown in FIG. 1.

For automated applications, it may be desirable to include means for determining whether a sample tube 300 is present in or absent from a particular sample tube receiving area 60 prior to pipetting. This can be achieved in the present invention by providing a machine readable label 140 to the lower support wall 40 above each sample tube receiving area 60, as indicated in FIGS. 6 and 20. If the sample tube 300 inserted into a sample tube receiving area 60 is sufficiently translucent, a machine for reading the labels 140, such as a bar code scanner, will be unable to read or detect the label behind the sample tube 300. Based its failure to read or detect a label 140, the machine can communicate to a computer controlling the operation of an associated automated sampling system, (see, e.g., FIG. 21), that a sample tube 300 is present in that particular sample tube receiving area 60. As a result, a robotic pipettor (not shown) associated with the automated sampling system will be instructed draw a predetermined amount of sample from the sample tube 300 at that location. But, if a sample tube 300 is absent from a sample tube receiving area 60, a reading machine associated with the automated sampling system will be able to read or detect the corresponding label 140 and will communicate to the computer that a sample tube 300 is not present in that sample tube receiving area. Accordingly, no instruction will be given to the robotic pipettor to draw sample from the sample tube 300 at that location.

Figure 21:
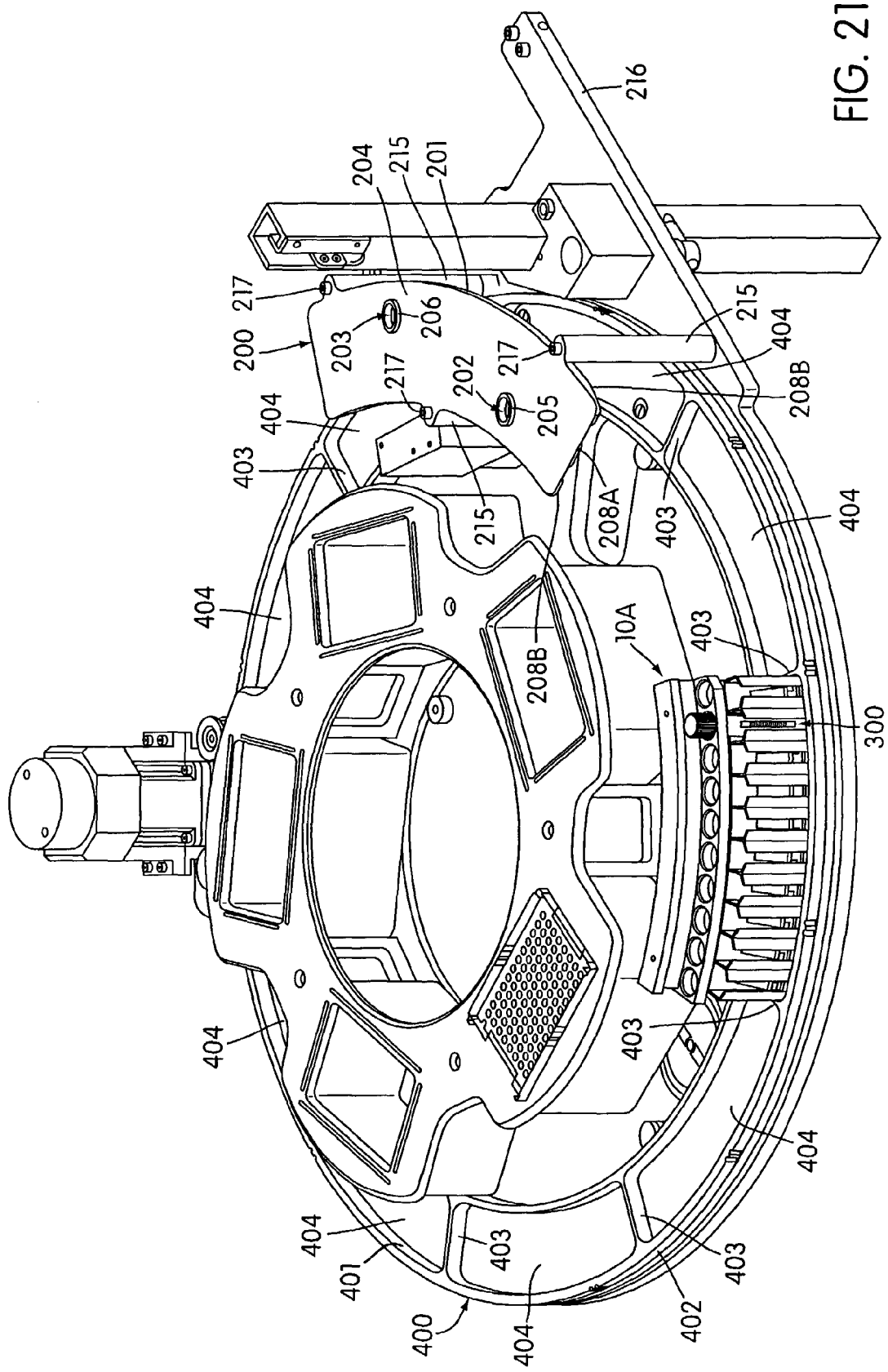
FIG. 21 shows the sample carrier of FIG. 1 positioned on a sample carousel and holding a single sample tube.

The base 30, 130 of the sample carrier 10 may be adapted for use with a sample carrier conveying means, such as a sample carousel for rotating a plurality of sample carriers within an automated sampling system. One such sample carousel 400 is disclosed by Ammann et al. in U.S. Pat. No. 6,335,166 and is illustrated in FIG. 21. This particular sample carousel 400 is formed of milled, unhardened aluminum and includes an annular trough 401 about the periphery of a ring 402 and a plurality of raised, radially extending dividers 403. The dividers 403 divide the trough 401 into nine arcuate sample carrier receiving wells 404 which can be configured to accommodate the sample carriers 10 of the present invention. The individual sample carrier receiving wells 404 are dimensioned to maintain the sample carriers 10 in an upright position as sample tubes 300 held by the sample carriers 10 are indexed under a robotic pipettor (not shown) for retrieving sample material for analysis. To track individual sample carriers 10 on the sample carousel 400, a machine readable label 120 (e.g., scannable bar code), can be provided to at least one end wall 63 or to a plate 110 attached to the sample tube blocking member 70, as described above and shown in FIG. 14.

Figure 22:
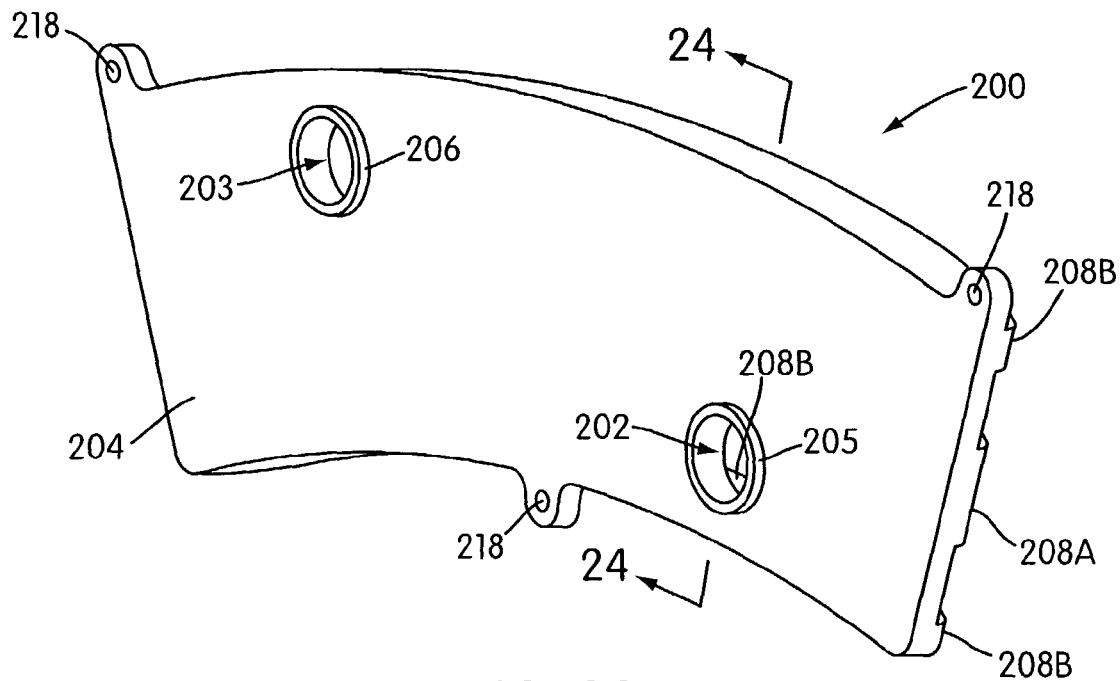
FIG. 22 is a perspective top view of a drip shield for use in an automated sampling system according to the present invention.
Figure 24:
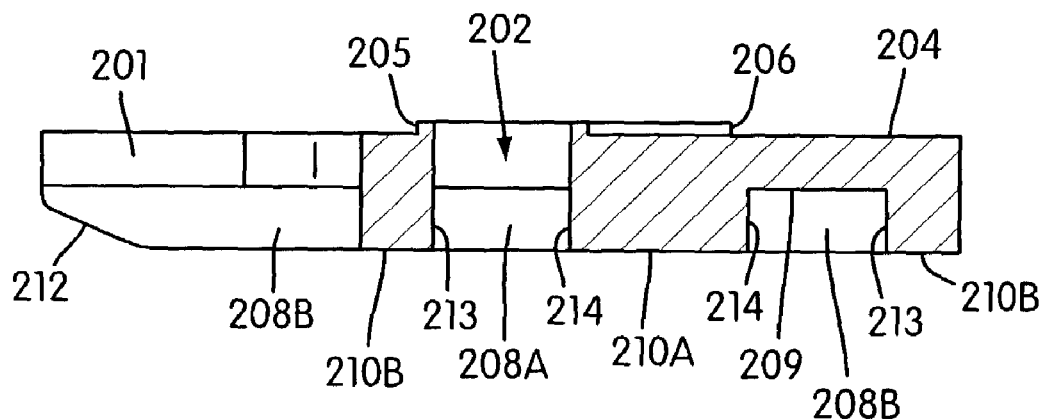
FIG. 24 is a section end view of the drip shield of FIG. 22, taken along the 24—24 line thereof.
Figure 25:
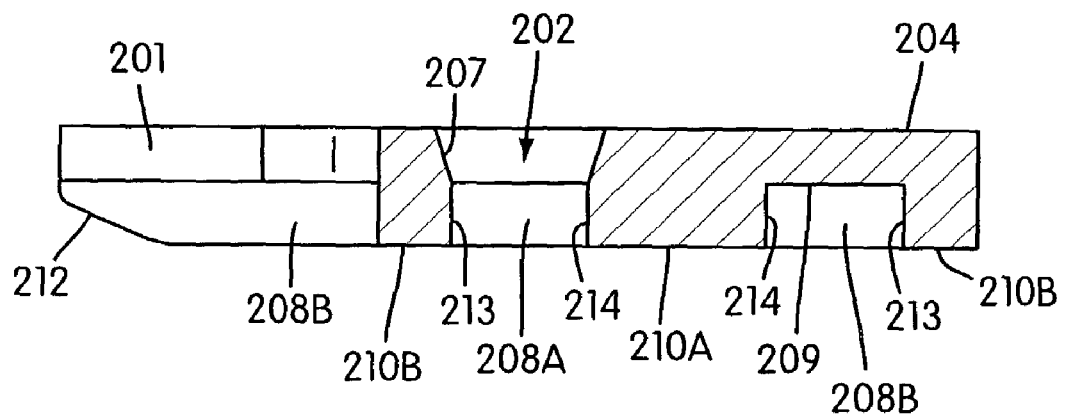
FIG. 25 is a section end view of an alternative drip shield for use in an automated sampling system according to the present invention.

The sample carriers 10 of the present invention can be used in combination with a device for protecting sample tubes 300 during sampling to further limit opportunities for cross-contamination. Such a device is provided by a novel drip shield 200 depicted in FIGS. 21–26. This drip shield 200 includes a cover plate 201 which is dimensioned to form a canopy over a sample carrier 10 fully contained thereunder. Thus, in a preferred embodiment, the drip shield 200 has an arcuate shape corresponding to the preferred arcuate shape of the sample carrier 10, as shown in FIG. 21. A minimum of two through-holes, identified in FIGS. 21–23 as a first through-hole 202 and a second through-hole 203, extend through the drip shield 200 and provide access to sample tubes 300 centered below the through-holes. The through-holes 202, 203 are dimensioned to permit non-interfering passage therethrough by pipette tips carried by a robotic pipettor, but are small enough so that a top surface 204 of the drip shield 200 can function to catch hanging droplets which are dislodged from the pipette tips during sample transfer procedures. Therefore, the diameters of the first and second through-holes 202, 203, respectively, are preferably about the same as or less than the smallest diameter of any cap 310 of a sample tube 300 to be carried by a sample carrier 10. Raised annular rims 205, 206 can be provided about the periphery of the first and second through-holes 202, 203, respectively, to impede fluid collected on the top surface 204 of the cover plate 201 from spilling into any of the sample tubes 300, as shown in FIGS. 22 and 24. In a preferred embodiment illustrated in FIG. 25, however, the top surface 204 of the cover plate 201 includes a chamfered ring 207 about the periphery of the first and second through-holes 202, 203, respectively, to aid in redirecting misaligned pipette tips.

The through-holes 202, 203 are arranged on the drip shield 200 so that the first through-hole 202 is positioned above a first or inner row of longitudinally or arcuately aligned sample tubes 300 and the second through-hole 203 is aligned above a second or outer row of longitudinally or arcuately aligned sample tubes. As the sample carrier 10 is indexed forward under the drip shield 200 by the sample carousel 400, the next sample tube 300 in each row of tubes can be presented under one of the through-holes 202, 203 for access by a robotic pipettor. An example of a robotic pipettor for use with the present invention is the Robotic Sample Processor, Model No. RSP9000, available from Cavro, Inc. of Sunnyvale, Calif. The through-holes 202, 203 are preferably offset on the drip shield 200 to further minimize opportunities for contamination resulting from released hanging droplets of sample. In a preferred mode, the through-holes 202, 203 are arranged on the drip shield 200, as shown in FIG. 21, so that the third sample tube 200 in the second or outer row of aligned tubes is being sampled as the first sample tube in the first or inner row of aligned tubes is being sampled.

Figure 23:
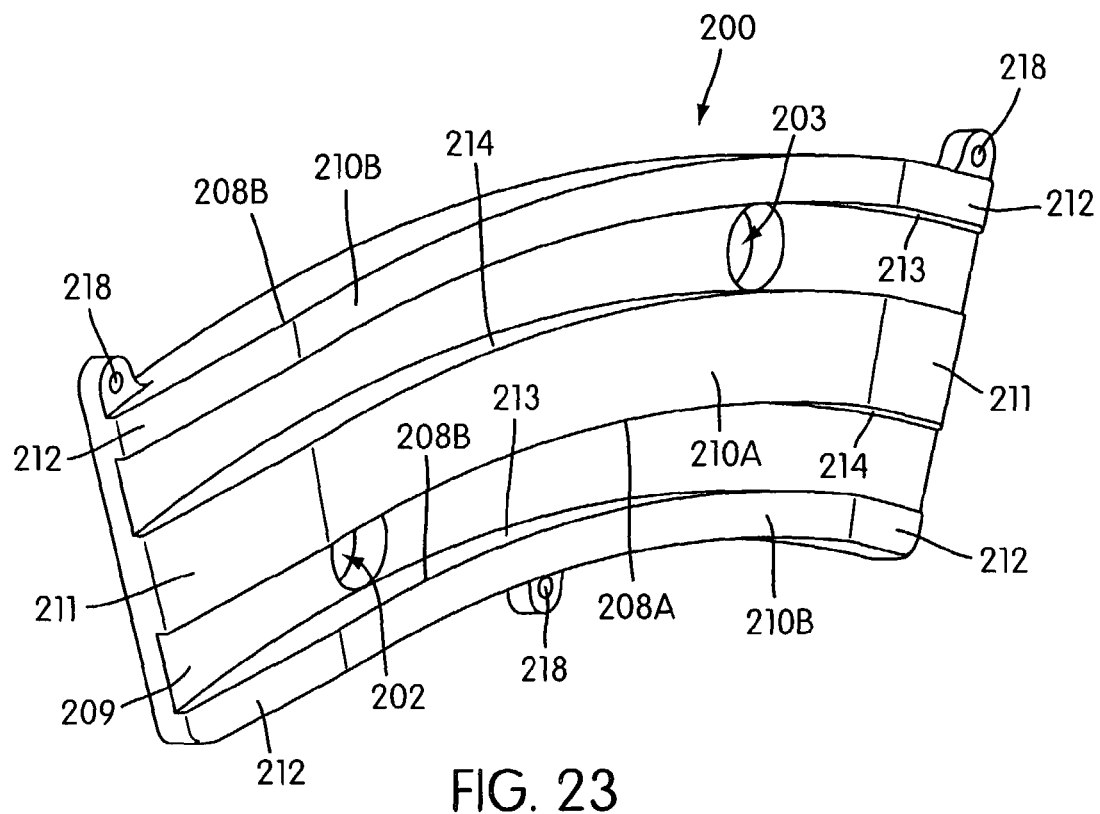
FIG. 23 is a perspective bottom view of the drip shield of FIG. 22.
Figure 26:
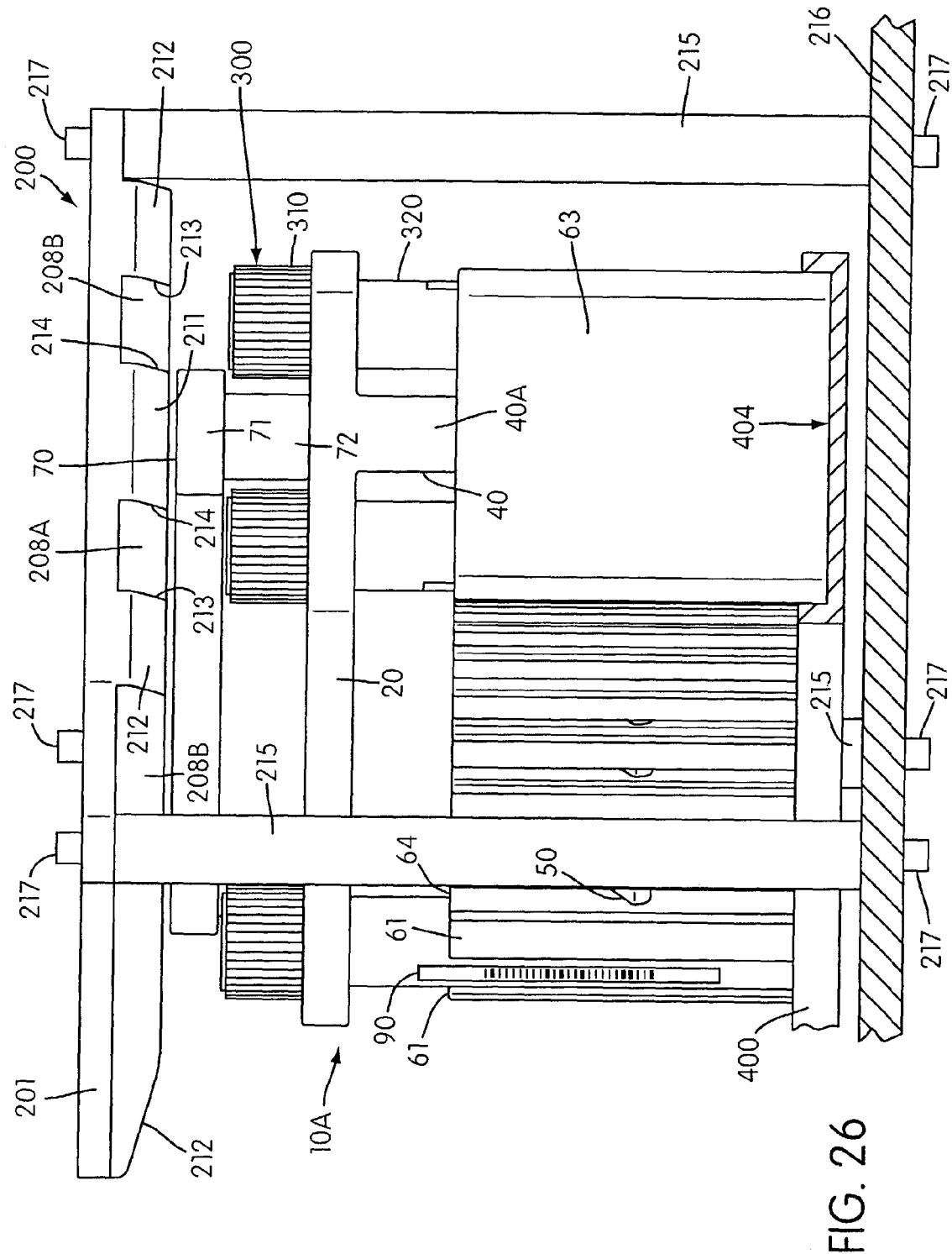
FIG. 26 is a section end view of the sample carrier of FIG. 1 carried under the drip shield of FIG. 22 by the sample carousel of FIG. 21.

When the drip shield 200 is employed in an automated sampling system, the drip shield preferably includes a series of three longitudinally or arcuately extending runners 208 which are spaced apart from each other and depend from a bottom surface 209 of the drip shield, as illustrated in FIG. 23. (The reference number "208" refers generally to all three runners shown in the figures, whereas the reference number "208A" refers to the inner runner and the reference number "208B" refers to the two outer runners.) The inner runner 208A is constructed and arranged on the bottom surface 209 of the drip shield 200 to limit vertical movement of the sample carrier 10 under the drip shield, as illustrated in FIG. 26. Vertical movement of the sample carrier 10 is of particular concern when a robotic pipettor is used to withdraw test sample from sample tubes 300 having penetrable caps 310. Depending on the withdrawal force required, it may be possible for a pipette tip mounted on a robotic pipettor to become snagged on the penetrable components of the cap 310 as the pipette tip is being withdrawn from the sample tube 300. As a consequence, a portion of the sample carrier 10 may be lifted from, and possibly relocated on, the sample carrousel 400 by the robotic pipettor. Therefore, to limit vertical movement of the sample carrier 10 under the drip shield 200, the distance between a bottom surface 210 of the inner runner 208A and a top surface 79 of the blocking wall 71 of the sample tube blocking member 70 is less than the vertical distance needed to extract or displace at least a portion of the sample carrier from its location on the sample carousel 400 (e.g., less than the depth of the sample carousel receiving well 404). Vertical relocation of a sample carrier 10 may occur when the retention force of a sample tube 300 (i.e., the cap component 310) applied to a pipette tip being withdrawn from the sample tube exceeds the holding force of a spring 50 or springs 150 applied to the sample tube. Preferably, the distance between the bottom surface 210 of the inner runner 208A and the top surface 79 of the blocking wall 71 of the sample tube blocking member 70 is no more than about 0.125 inches (3.18 mm). The inner runner 208A can also function as a barrier to carryover contamination between sample tubes 300 held in sample tube receiving areas 60 on opposite sides of the lower support wall 40 of the sample carrier 10.

The preferred runners 208A, 208B have tapered ends 211, 212, respectively, as shown in FIG. 23. The tapered ends 211 of the inner runner 208A are provided to facilitate proper seating of sample carriers 10 which have not been fully inserted into sample carousel receiving wells 404 prior to rotation, whether the sample carousel 400 is being rotated clockwise or counterclockwise. The outer runners 208B are spaced-apart from the inner runner 208A such that inner side walls 213 of the outer runners 208B and both side walls 214 of the inner runner 208B are positioned vertically above and overhang sample tubes 300 which are held by the sample carrier 10 and positioned beneath the drip shield 200, as shown in FIG. 26. Opposed side walls 213, 214 of the runners 208A, 208B preferably do not extend beyond the periphery of the through-holes 202, 203 of the drip shield 200, thereby permitting non-interfering passage of fluid transverse devices through the through-holes 213, 214. In this way, the runners 208 function as an additional failsafe for blocking vertical movement of sample tubes 300 held by the sample carrier 10 in the event that a sample tube is unexpectedly extracted beyond the sample tube blocking member 70 during pipetting.

The drip shield 200 can be maintained in fixed relationship over sample carriers 10 being indexed on the sample carousel 400 therebelow by means of mounting posts 215 fixed to a stationary surface 216 of the automated sampling system, as illustrated in FIG. 21 and more fully described by Ammann et al. in U.S. Pat. No. 6,335,166. The drip shield 200 can be secured to these mounting posts 215 using screws, bolts or like mechanical fasteners. Preferred are bolts 217 mated with threaded holes (not shown) in the mounting posts 215 and inserted through three through-holes 218 located on the periphery of the drip shield 200, as shown in FIG. 21.

Sample carriers 10 and drip shields 200 of the present invention are preferably made of a substantially non-conductive plastic, such as acrylonitrile-butadiene-styrene (ABS), which can be obtained from GE Plastics of Pittsfield, Mass. as Cycolac® MG47. The materials used should be selected to resist corrosion by chemicals and reagents that the sample carrier 10 and drip shield 200 may be exposed to during use. The drip shield 200 and the sample tube blocking member 70, the transverse wall 20 and the upper portion 40A of the lower support wall 40 of the preferred sample carrier 10A are preferably machined components. The remainder of the components of the preferred sample carrier 10A are preferably formed by injection molding procedures known to those skilled in the art.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

We claim:

1. A sample carrier for use in holding and containing a plurality of sample tubes for access by a fluid transfer device, the sample carrier comprising:
   a lower support wall;
   a base joined to a bottom end of the lower support wall;
   a plurality of sample tube receiving areas adjacent the lower support wall for receiving and holding a plurality of sample tubes in substantially vertical orientations; and
   a sample tube blocking member that is provided to and registered with the lower support wall opposite the base, wherein the sample tube blocking member comprises a blocking wall that extends laterally over only a portion of each of the sample tube receiving areas.

2. The sample carrier of claim 1, wherein said sample carrier further comprises one or more springs disposed within each of the sample tube receiving areas for holding a corresponding sample tube therein.

3. The sample carrier of claim 2, wherein each of the sample tube receiving areas is defined by:
   a pair of fixed partitions, each partition having a generally perpendicular or radial orientation relative to the lower support wall; and
   one or more fixed retaining walls having an opposed orientation relative to the lower support wall.

4. The sample carrier of claim 3, wherein each partition separating adjacent sample tube receiving areas and a pair of retaining walls are joined to form a Y-shaped divider.

5. The sample carrier of claim 4, wherein the partitions which are adjacent to only one sample tube receiving area and their associated retaining walls form a pair of end walls.

6. The sample carrier of claim 3, wherein the one or more springs comprise a leaf spring fixed by and extending outward relative to the lower support wall and into one of the sample tube receiving areas, wherein the leaf spring is configured and arranged to bias a sample tube against the one or more retaining walls associated with the corresponding sample tube receiving area.

7. The sample carrier of claim 6, wherein the leaf spring extends outward through a slot formed in the lower support wall.

8. The sample carrier of claim 1, wherein each sample tube receiving area comprises a slot formed in the base which is configured to receive a sample tube therein.

9. The sample carrier of claim 8, wherein an opening extends through an outer surface of the base adjacent the slot to permit viewing of machine readable information affixed to an outer surfaces of a sample tubes held by the slot.

10. The sample carrier of claim 1, wherein the sample tube blocking member further comprises an upper support wall depending from the blocking wall, and wherein the upper support wall is provided to the lower support wall.

11. The sample carrier of claim 10, wherein the lower support wall and the upper support wall comprise mated first and second registration elements, respectively, for registering the sample tube blocking member with the lower support wall.

12. The sample carrier of claim 11, wherein the first registration elements comprise a pair of pins extending upward from a top surface of the lower support wall, and wherein the second registration elements comprise a pair of corresponding through-holes in the upper support wall for receiving the pins therethrough.

13. The sample carrier of claim 1, wherein the sample carrier includes a plurality of sample tube receiving areas adjacent opposite sides of the lower support wall.

14. The sample carrier of claim 13, wherein the sample carrier has an arcuate shape.

15. A sample carrier for use in holding and containing a plurality of sample tubes for access by a fluid transfer device, the sample carrier comprising:
   a lower support wall;
   a base joined to a bottom end of the lower support wall;
   a plurality of sample tube receiving areas adjacent the lower support wall for receiving and holding a plurality of sample tubes in substantially vertical orientations;
   a transverse wall joined to an upper portion of the lower support wall and having a plurality of spaced-apart openings, wherein each opening is dimensioned to receive a sample tube therethrough, and wherein the openings are aligned with the sample tube receiving areas to maintain sample tubes held by the sample carrier in substantially vertical orientations; and
   a sample tube blocking member that is provided to and registered with a top end of the transverse wall, and wherein the sample tube blocking member comprises a blocking wall that extends laterally over only a portion of each of the sample tube receiving areas.

16. The sample carrier of claim 15, wherein the sample tube blocking member comprises an upper support wall depending from the blocking wall and in touching contact with the top end of the transverse wall.

17. The sample carrier of claim 15, wherein said sample carrier further comprises one or more springs disposed within each of the sample tube receiving areas for holding a corresponding sample tube therein.

18. The sample carrier of claim 17, wherein each of the sample tube receiving areas is defined by:
   a pair of fixed partitions, each partition having a generally perpendicular or radial orientation relative to the lower support wall; and
   one or more fixed retaining walls having an opposed orientation relative to the lower support wall.

19. The sample carrier of claim 18, wherein each partition separating adjacent sample tube receiving areas and a pair of retaining walls are joined to form a Y-shaped divider.

20. The sample carrier of claim 19, wherein the partitions which are adjacent to only one sample tube receiving area and their associated retaining walls form a pair of end walls.

21. The sample carrier of claim 18, wherein the one or more springs comprise a leaf spring fixed by and extending outward relative to the lower support wall and into one of the sample tube receiving areas, wherein the leaf spring is configured and arranged to bias a sample tube against the one or more retaining walls associated with the corresponding sample tube receiving area.

22. The sample carrier of claim 21, wherein the leaf spring extends outward through a slot formed in the lower support wall.

23. The sample carrier of claim 15, wherein:
   the lower support wall comprises upper and lower portions; and
   the sample tube receiving areas comprise a laterally extending wall positioned between and joined to the upper and lower portions of the lower support wall, wherein the laterally extending wall comprises a plurality of spaced-apart openings substantially axially aligned with the openings in the transverse wall, each opening in the laterally extending wall being sized to receive a sample tube therethrough, and wherein a set of finger springs depends from a bottom surface of the laterally extending wall about the periphery of each opening, each set of finger springs being configured and arranged to hold a sample tube within the corresponding opening.

24. The sample carrier of claim 23, wherein the lower support wall and the laterally extending wall form an integral piece.

25. The sample carrier of claim 23, wherein each set of finger springs includes four finger springs.

26. The sample carrier of claim 23, wherein each finger spring includes a distal node to facilitate removal of the sample tubes from the sample tube holding receiving areas.

27. The sample carrier of claim 15, wherein the transverse wall and the sampled tube blocking member comprise mated first and second registration elements, respectively, for registering the sample tube blocking member with the transverse wall.

28. The sample carrier of claim 27, wherein the first registration elements comprise a pair pins extending upward from a top surface of the transverse wall, and wherein the second registration elements comprise a pair of corresponding through-holes in the sample tube blocking member for receiving the pins therethrough.

29. The sample carrier of claim 15, wherein a top surface of the transverse wall is chamfered about the periphery of each opening.

30. The sample carrier of claim 15 further comprising one or more sample tubes held by the sample tube receiving areas, wherein a cap component associated with each sample tube is at least partially contained within the corresponding opening between top and bottom surfaces of the transverse wall.

31. The sample carrier of claim 30, wherein each cap includes a seal capable of being penetrated by a plastic pipette tip..

32. The sample carrier of claim 30, wherein the longitudinal axis of the cap component associated with each sample tube is no more than about 0.125 inches from the longitudinal axis of the corresponding opening in the transverse wall.

33. The sample carrier of claim 15, wherein the sample carrier includes a plurality of sample tube receiving areas adjacent opposite sides of the lower support wall.

34. The sample carrier of claim 33, wherein the sample carrier has an arcuate shape.

35. The sample carrier of claim 1 further comprising one or more sample tubes held by the sample tube receiving areas, wherein the blocking wall extends over only a portion of each of the sample tubes held by the sample tube receiving areas, thereby limiting vertical movement of the sample tubes held by the sample carrier without obstructing access to the contents of the sample tubes by a fluid transfer device.

36. The sample carrier of claim 3 further comprising one or more sample tubes held by the sample tube receiving areas, wherein the blocking wall extends over only a portion of each of the sample tubes held by the sample tube receiving areas, thereby limiting vertical movement of the sample tubes held by the sample carrier without obstructing access to the contents of the sample tubes by a fluid transfer device.

37. The sample carrier of claim 8 further comprising one or more sample tubes held by the sample tube receiving areas, wherein the blocking wall extends over only a portion of each of the sample tubes held by the sample tube receiving areas, thereby limiting vertical movement of the sample tubes held by the sample carrier with out obstructing access to the contents of the sample tubes by a fluid transfer device.

38. The sampler carrier of claim 15 further comprising one or more sample tubes held by the sample tube receiving areas, wherein the blocking wall extends over only a portion of each of the sample tubes held by the sample tube receiving areas, thereby limiting vertical movement of the sample tubes held by the sample carrier without obstructing access to the contents of the sample tubes by a fluid transfer device.

39. The sample carrier of claim 18 further comprising one or more sample tubes held by the sample tube receiving areas, wherein the blocking wall extends over only a portion of each of the sample tubes held by the sample tube receiving areas, thereby limiting vertical movement of the sample tubes held by the sample carrier without obstructing access to the contents of the sample tubes by a fluid transfer device.

40. The sample carrier of claim 21 further comprising one or more sample tubes held by the sample tube receiving areas, whererin the blocking wall extends over only a portion of each of the sample tubes held by the sample tube receiving areas, thereby limiting vertical movement of the sample tubes held by the sample carrier without obstructing access to the contents of the sample tubes by a fluid transfer device.

41. The sample carrier of claim 23 further comprising one or more sample tubes held by the sample tube receiving areas, wherein the blocking wall extends over only a portion of each of the sample tubes held by the sample tube receiving areas, thereby limiting vertical movement of the sample tubes held by the sample carrier witout obstructing access to the contents of the sample tubes by a fluid transfer device.

* * * * *